United States Patent [19]

Raddatz et al.

[11] Patent Number: 5,304,563

[45] Date of Patent: Apr. 19, 1994

[54] 2-SUBSTITUTED QUINOLINES, AND THEIR USE IN MEDICAMENTS

[75] Inventors: Siegfried Raddatz, Cologne; Klaus-Helmut Mohrs; Michael Matzke, both of Wuppertal; Romanis Fruchtmann, Cologne; Armin Hatzelmann, Constance; Christian Kohlsdorfer, Erftstadt; Reiner Müller-Peddinghaus, Bergisch Galdbach; Pia Theisen-Popp, Aachen, all of Fed. Rep. of Germany

[73] Assignee: Bayer Aktiengesellschaft, Leverkusen, Fed. Rep. of Germany

[21] Appl. No.: 967,881

[22] Filed: Oct. 28, 1992

Related U.S. Application Data

[63] Continuation-in-part of Ser. No. 834,734, Feb. 12, 1992.

[30] Foreign Application Priority Data

Feb. 22, 1991 [DE] Fed. Rep. of Germany ....... 4105551
Aug. 12, 1992 [DE] Fed. Rep. of Germany ....... 4226649

[51] Int. Cl.$^5$ ................. C07D 403/06; C07D 215/48; A61K 31/47; A61K 31/505
[52] U.S. Cl. .................................. 514/311; 514/314; 514/255; 514/256; 546/172; 546/174; 546/175; 544/336; 544/242
[58] Field of Search .................. 546/175, 172, 174; 514/311, 314, 255, 256; 544/336, 242

[56] References Cited

U.S. PATENT DOCUMENTS

| | | | |
|---|---|---|---|
| 4,929,626 | 5/1990 | Mohrs et al. | 514/311 |
| 4,970,215 | 11/1990 | Mohrs et al. | 514/311 |
| 5,091,392 | 2/1992 | Raddatz et al. | 514/311 |

FOREIGN PATENT DOCUMENTS

| | | |
|---|---|---|
| 0219308 | 10/1986 | European Pat. Off. . |
| 0339416 | 4/1989 | European Pat. Off. . |
| 0344519 | 5/1989 | European Pat. Off. . |
| 0344519 | 12/1989 | European Pat. Off. . |
| 0399291 | 5/1990 | European Pat. Off. . |
| 0414076 | 8/1990 | European Pat. Off. . |
| 0414078 | 8/1990 | European Pat. Off. . |
| 0399291 | 11/1990 | European Pat. Off. . |
| 0499926 | 8/1992 | European Pat. Off. . |
| 0509359 | 10/1992 | European Pat. Off. . |

OTHER PUBLICATIONS

Henri Ulrich, "The Reaction of Sulfonylureas and Sulfonamides with Carbonyl Chloride. A New Synthesis of Isocynates," *J. Org. Chem.*, 1966, pp. 2658–2661.

Gunter E. Jeromin, "Seitenkettenchlorierungen von N–Heterocyclen mit Trichlorisocyanursaure," in *Chem. Bes.*, 120, 1987, pp. 649–651.

John C. Sheehan, "Total Synthesis of a Monocyclic Peptide Lactone Antibiotic, Etamycin," in Journal of the Am. Chem. Soc., 1973, pp. 875–879.

Gerd Utermann, "Genetic Variants of Group A Apolipoproteins," in *The Journal of Biological Chemistry*, Jan. 10, 1982, pp. 501–507.

N. Leo Benoiton, "A Series of Lysyldipeptide Derivatives for Racemization Studies in Peptide Synthesis," in *Int. J. Peptide Res.*, 1979, pp. 403–408.

N. Leon Benoiton, "Studies on Racemization During Couplings Using a Series of Model Tripeptides Involving Activates Residues with Unfunctionalized Side Chains," in *J. Peptide Protein Res.*, 1981, pp. 197–204.

"Trimethylcyclohexande," in *Beilstein's* BANO V, pp. 43, 29, 15 and 109, (1922).

Pierre Borgeat, "Arachidonic acid metabolism in polymorphonuclear Leukocytes: Effects of ionophore A23187," in *Prac. Natl. Acad. Sci. USA*, May 1979, pp. 2148–2152.

*Primary Examiner*—David B. Springer
*Attorney, Agent, or Firm*—Sprung Horn Kramer & Woods

[57] ABSTRACT

The title compounds are prepared either by reacting the corresponding halogenomethylquinolines with substituted phenols, optionally subsequently alkylating these or hydrolysing esters to acids, or by reacting phenyl-substituted quinolinecarboxylic acid derivatives with sulphonamides. The new phenyl-substituted quinolines are utilizable as active substances in medicaments, in particular as lipoxygenase inhibitors.

15 Claims, No Drawings

2-SUBSTITUTED QUINOLINES, AND THEIR USE IN MEDICAMENTS

This is a continuation-in-part of application Ser. No. 834,734, filed Feb. 12, 1992, now pending.

The present invention relates to 2-substituted quinolines, processes for their preparation and their use in medicaments.

Substituted 4-(quinolin-2-yl-methoxy)phenylacetic acid derivatives and α-substituted 4-(quinolin-2-yl-methoxy)phenylacetic acid derivatives have been disclosed in EP 344,519 (U.S. Pat. No. 4,970,215) and EP 339,416.

The present invention now relates to 2-substituted quinolines of the general formula (I)

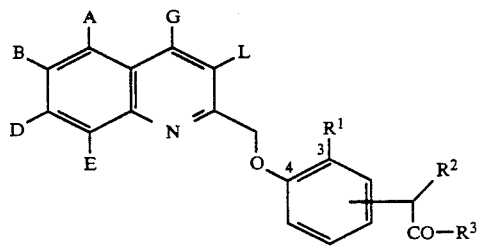

in which
A, B, D, E, G and L are identical or different and represent hydrogen, hydroxyl, halogen, cyano, carboxyl, nitro, trifluoromethyl, trifluoromethoxy or
straight-chain or branched alkyl or alkoxy each having up to 8 carbon atoms, or
represent aryl having 6 to 10 carbon atoms, which is optionally substituted by halogen, hydroxyl, nitro or cyano,
$R^1$ represents halogen, cyano, nitro, azido, trifluoromethyl, trifluoromethoxy or trifluoromethylthio, or
represents straight-chain or branched alkoxy or acyl each having up to 8 carbon atoms, or
represents straight-chain or branched alkyl having up to 8 carbon atoms, which is optionally substituted by hydroxyl or alkoxy having up to 6 carbon atoms, or
represents aryl having 6 to 10 carbon atoms, or
represents straight-chain or branched alkenyl having up to 6 carbon atoms, or
represents a group of the formula $-NR^4R^5$,
in which
$R^4$ and $R^5$ are identical or different and denote hydrogen, straight-chain or branched alkyl having up to 8 carbon atoms, phenyl, acetyl or benzoyl, or
represents a saturated or unsaturated, optionally substituted 5- or 6-membered heterocycle having up to 3 hetero atoms from the series comprising sulphur, oxygen and nitrogen,
$R^2$ represents cycloalkyl or -alkenyl having 3 to 12 carbon atoms,
$R^3$ represents a radical of the formula $-OR^6$ or $-NR^7-SO_2-R^8$,
in which
$R^6$ denotes hydrogen, straight-chain or branched alkyl having up to 8 carbon atoms, or phenyl,
$R^7$ denotes hydrogen or straight-chain or branched alkyl having up to 6 carbon atoms,
$R^8$ denotes aryl having 6 to 10 carbon atoms, which is optionally mono- or disubstituted by identical or different substituents from the series comprising halogen, cyano, hydroxyl, nitro, trifluoromethyl, trifluoromethoxy, trifluoromethylthio, or by straight-chain or branched alkyl or alkoxy each having up to 8 carbon atoms, or denotes straight-chain or branched alkyl having up to 8 carbon atoms, which is optionally substituted by phenyl, which in turn can be substituted by halogen, cyano, nitro, trifluoromethyl, trifluoromethoxy, trifluoromethylthio or hydroxyl, or by straight-chain or branched alkyl or alkoxy each having up to 6 carbon atoms
and their physiologically acceptable salts. 5- and 6-membered heterocycles which are mentioned as preferred are those having up to 2 nitrogen atoms such as, for example, pyrryl, pyrazolyl, pyridyl, pyrimidyl, pyrazinyl or pyridazinyl, or furyl or thienyl.

In the context of the present invention, physiologically acceptable salts are preferred. Physiologically acceptable salts of the 2-substituted quinolines may be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are moreover salts of the monovalent metals such as alkali metals and the ammonium salts. Sodium salts, potassium salts and ammonium salts are preferred.

The compounds according to the invention exist in stereoisomeric forms which behave either as image and mirror image (enantiomers), or which do not behave as image and mirror image (diastereomers). The invention relates both to the antipodes and to the racemic forms as well as the diastereomer mixtures. The racemic forms, like the diastereomers, can be separated into the stereoisomerically uniform constituents in a known manner [cf. E. L. Eliel, Stereochemistry of Carbon Compounds, McGraw Hill, 1962].

Preferred compounds of the general formula (I) are those
in which
A, B, D, E, G and L are identical or different and represent hydrogen, hydroxyl, fluorine, chlorine, bromine, carboxyl, nitro, trifluoromethyl, trifluoromethoxy or
represent straight-chain or branched alkyl or alkoxy each having up to 6 carbon atoms, or
represent phenyl which is optionally substituted by fluorine, chlorine, bromine, hydroxyl, nitro or cyano,
$R^1$ represents fluorine, chlorine, bromine, iodine, cyano, nitro, azido, trifluoromethyl, trifluoromethoxy, or
represents straight-chain or branched alkoxy or acyl each having up to 6 carbon atoms, or
represents straight-chain or branched alkyl having up to 6 carbon atoms, which is optionally substituted by hydroxyl or alkoxy having up to 4 carbon atoms, or represents straight-chain or branched alkenyl having up to 4 carbon atoms, or
represents a group of the formula —NR$^4$R$^5$,
in which
R$^4$ and R$^5$ are identical or different and denote hydrogen or straight-chain or branched alkyl having up to 4 carbon atoms,
or represent pyrryl, pyridyl, furyl or phenyl,
R$^2$ represents cycloalkyl having 3 to 12 carbon atoms,
R$^3$ represents a radical of the formula —OR$^6$ or —NR$^7$—SO$_2$—R$^8$,
in which
R$^6$ denotes hydrogen or straight-chain or branched alkyl having up to 6 carbon atoms,
R$^7$ denotes hydrogen or straight-chain or branched alkyl having up to 4 carbon atoms,
R$^8$ denotes phenyl which is optionally substituted by fluorine, chlorine, bromine, iodine, cyano or by straight-chain or branched alkyl or alkoxy each having up to 6 carbon atoms, or denotes straight-chain or branched alkyl having up to 6 carbon atoms, which is optionally substituted by phenyl which can in turn be substituted by fluorine, chlorine, bromine or trifluoromethyl or by straight-chain or branched alkyl or alkoxy each having up to 4 carbon atoms
and their physiologically acceptable salts.

Particularly preferred compounds of the general formula (I) are those
in which
A, B, D, E, G and L are identical or different and represent hydrogen, hydroxyl, fluorine, chlorine, bromine or straight-chain or branched alkyl having up to 4 carbon atoms,
R$^1$ represents fluorine, chlorine, bromine, nitro, azido or trifluoromethoxy, or
represents straight-chain or branched alkoxy or acyl each having up to 4 carbon atoms, or
represents straight-chain or branched alkyl having up to 4 carbon atoms, which is optionally substituted by hydroxyl or methoxy, or
represents straight-chain or branched alkenyl having up to 4 carbon atoms, or
represents a group of the formula —NR$^4$R$^5$,
in which
R$^4$ and R$^5$ are identical or different and denote hydrogen or straight-chain or branched alkyl having up to 3 carbon atoms,
or represents pyrryl, furyl or phenyl,
R$^2$ represents cyclobutyl, cyclopentyl, cyclohexyl, cycloheptyl or cyclooctyl,
R$^3$ represents a radical of the formula —OR$^6$ or —NR$^7$—SO$_2$—R$^8$,
in which
R$^6$ denotes hydrogen or straight-chain or branched alkyl having up to 4 carbon atoms,
R$^7$ denotes hydrogen, methyl or ethyl,
R$^8$ denotes phenyl which is optionally substituted by methyl, fluorine, chlorine, bromine, iodine, methoxy or trifluoromethyl, or denotes straight-chain or branched alkyl having up to 4 carbon atoms, which is optionally substituted by phenyl which can in turn be substituted by fluorine, chlorine, bromine, methyl or methoxy
and their physiologically acceptable salts.

Very particularly preferred compounds of the formula (I) are those in which A, B, D, E, G and L represent hydrogen. Those compounds are also very particularly preferred in which the radical —CHR$^2$—COR$^3$ is in the 4-position relative to the quinolylmethoxy radical.

Processes for the preparation of the compounds of the general formula (I) according to the invention have additionally been found, characterised in that
[A] in the case where R$^3$ represents the group —OR$^6$
[A$_1$] either compounds of the general formula (IIa)

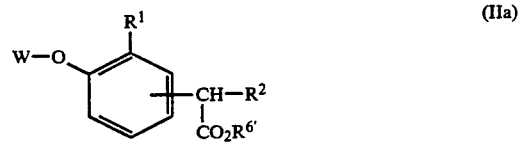

in which
R$^1$ and R$^2$ have the abovementioned meaning,
W represents a hydroxyl protective group such as benzyl or tert.-butyl, and
R$^{6'}$ has the abovementioned meaning of R$^6$ but does not represent hydrogen,
are converted, after elimination of the protective group, by etherification with 2-halogenomethylquinolines of the general formula (III)

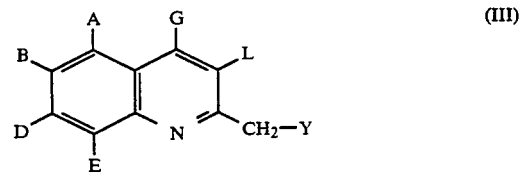

in which
A, B, D, E, G and L have the abovementioned meaning and
Y represents halogen, in particular chlorine or bromine,
in inert solvents into the compounds of the general formula (IVa)

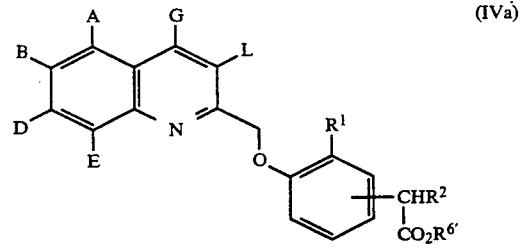

in which A, B, D, E, G, L, R$^1$, R$^2$ and R$^{6'}$ have the abovementioned meaning, and the latter in the case of the esters (R$^6 \neq$H) are then hydrolysed, or
[A$_2$] compounds of the general formula (IIb)

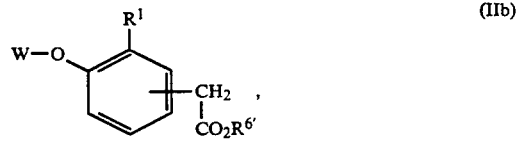

in which R$^1$ and R$^{6'}$ have the abovementioned meaning, are converted, after elimination of the protective group, initially by etherification with 2-halogenomethylquinolines of the general formula (III) in inert solvents into compounds of the general formula (IVb)

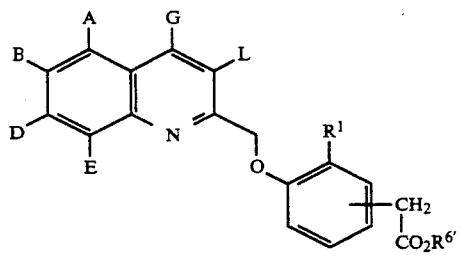

in which A, B, D, E, G, L, $R^1$ and $R^{6'}$ have the abovementioned meaning, and the latter are then alkylated with compounds of the general formula (V)

$$R^2\text{-}Z \qquad (V)$$

in which
$R^2$ has the abovementioned meaning and
Z represents chlorine, bromine or iodine,
in inert solvents and in the case of the esters ($R^6 \neq H$) the esters are hydrolysed or

[B] in the case where $R^3$ represents the group $-NR^7-SO_2R^8$, compounds of the general formula (IVc)

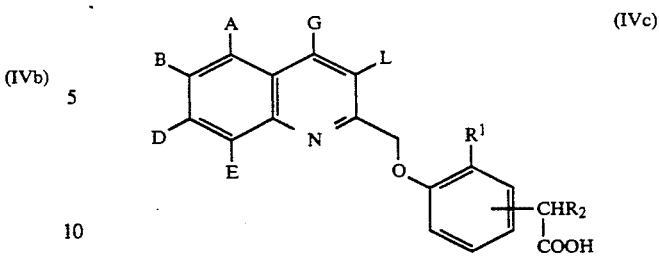

in which A, B, D, E, G, L, $R^1$ and $R^2$ have the abovementioned meaning, are amidated in inert solvents, if appropriate in the presence of a base, with sulphonamides of the general formula (VI)

$$HNR^7\text{—}SO_2R^8 \qquad (VI)$$

in which $R^7$ and $R^8$ have the abovementioned meaning, and

[C] in the case of the enantiomers the corresponding enantiomerically pure acids (IVc) are separated by a customary method and reacted further by the abovementioned processes, it being possible for the substituent $R^1$ to be varied in any of the abovementioned steps, optionally by customary chemical methods.

The processes according to the invention can be illustrated by way of example by the following reaction scheme:

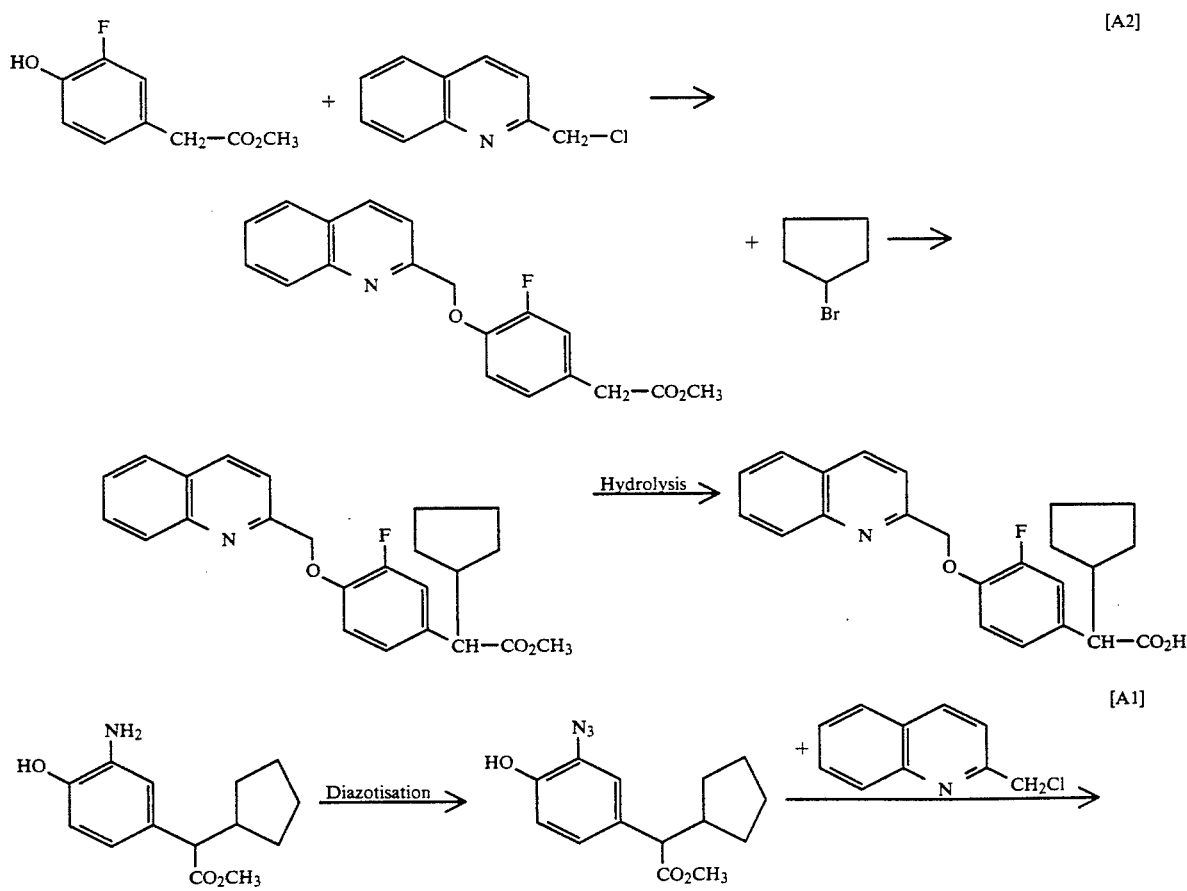

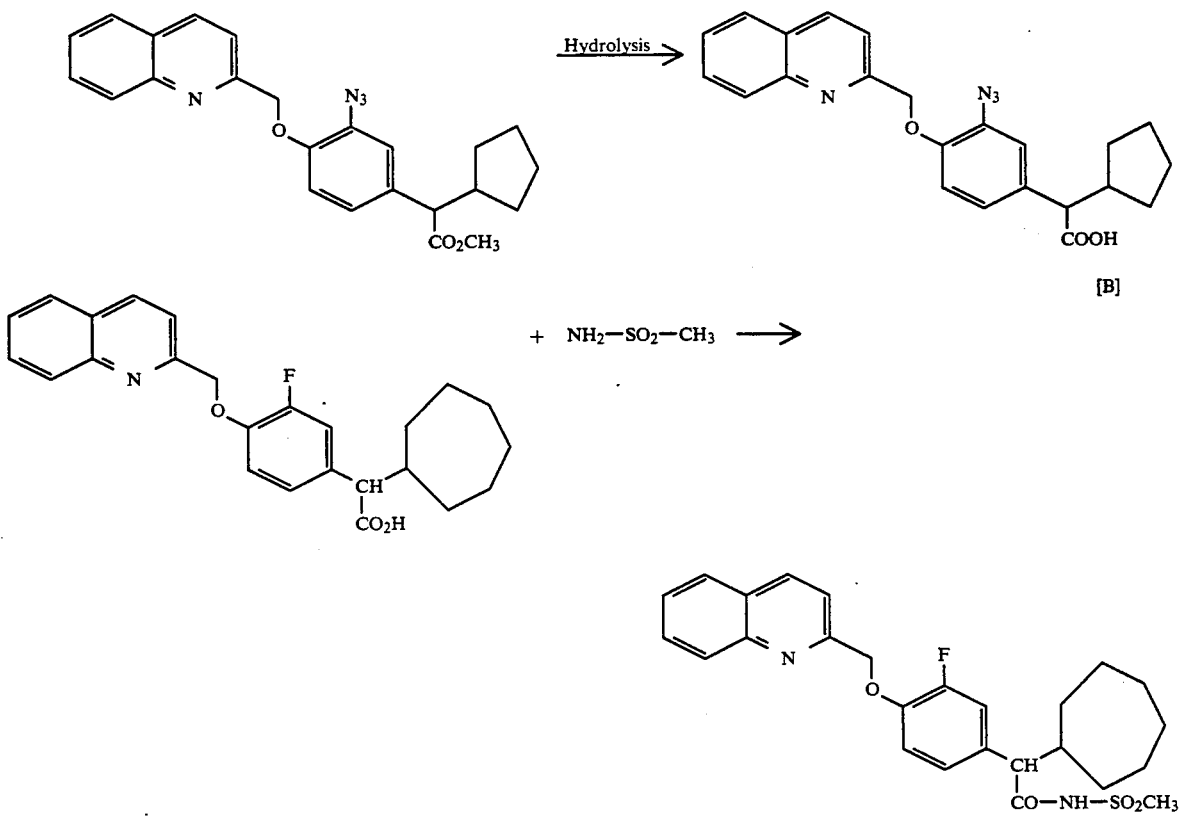

The elimination of the protective groups from the corresponding ethers (IIa) and (IIb) is carried out by a customary method, for example by hydrogenolytic cleavage of the benzyl ether in the abovementioned inert solvents in the presence of a catalyst with hydrogen gas [cf. additionally Th. Green: "Protective Groups in Organic Synthesis", J. Wiley & Sons, 1981, New York].

The etherification can be carried out in inert solvents, optionally in the presence of a base. Solvents for the etherification can be inert organic solvents which do not change under the reaction conditions. These preferably include ethers such as, for example, dioxane, tetrahydrofuran or diethyl ether, halogenohydrocarbons such as dichloromethane, trichloromethane, tetrachloromethane, 1,2-dichloroethane or trichloroethylene, hydrocarbons such as benzene, xylene, toluene, hexane, cyclohexane or petroleum fractions, nitromethane, dimethylformamide, acetonitrile, acetone or hexamethylphosphoric triamide. It is also possible to employ mixtures of these solvents.

Bases which can be employed for the etherification are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl($C_1$-$C_6$)amines) such as triethylamine, or heterocycles such as pyridine, methylpiperidine, piperidine or morpholine.

It is also possible to employ alkali metals such as sodium and its hydrides, such as sodium hydride, as bases.

The etherification is in general carried out in a temperature range from 0° C. to +150° C., preferably from +10° C. to +100° C.

The etherification is in general carried out at normal pressure. However, it is also possible to carry out the process at reduced pressure or elevated pressure (for example in a range from 0.5 to 5 bar).

In general, 0.5 to 5 mol, preferably 1 to 2 mol, of halide (III) are employed relative to 1 mol of the reaction component. The base is in general employed in an amount of 0.5 to 5 mol, preferably of 1 to 3 mol, relative to the halide.

The compounds of the general formula (IIa) and (IIb) are known per se or can be prepared by a customary method [cf. J. Org. Chem. 31, 2658 (1966)].

The compounds of the general formula (III) and their preparation are also known [cf. Chem. Ber. 120, 649 (1987)].

Suitable solvents for the process according to the invention and for the alkylation are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Dichloromethane is preferred.

The alkylation is carried out in the abovementioned solvents at temperatures from 0° C. to +150° C., preferably at room temperature to 100° C., and at normal pressure.

The amidation is in general carried out in inert solvents in the presence of a base and of a dehydrating agent.

Suitable solvents here are inert organic solvents which do not change under the reaction conditions. These include halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetonitrile or hexamethylphosphoric triamide. It is also possible to employ mixtures of the solvents mentioned. Dichloromethane is particularly preferred.

Suitable bases for the amidation are the customary basic compounds. These preferably include alkali metal hydroxides and alkaline earth metal hydroxides such as lithium hydroxide, sodium hydroxide, potassium hydroxide or barium hydroxide, alkali metal hydrides such as sodium hydride, alkali metal carbonates or alkaline earth metal carbonates such as sodium carbonate, potassium carbonate, or alkali metal alkoxides such as, for example, sodium methoxide or ethoxide, potassium methoxide or ethoxide or potassium tert.-butoxide, or organic amines such as benzyltrimethylammonium hydroxide, tetrabutylammonium hydroxide, pyridine, triethylamine or N-methylpiperidine.

The amidation is in general carried out in a temperature range from 0° C. to 150° C., preferably at 25° C. to 40° C.

The amidation is in general carried out at normal pressure. However, it is also possible to carry out the process at reduced pressure or at elevated pressure (for example in a range from 0.5 to 5 bar).

When carrying out the amidation, the base is in general employed in an amount of 1 to 3 mol, preferably of 1 to 1.5 mol, relative to 1 mol of the carboxylic acid (VIc).

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldimiidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl aminophosphonate or methanesulphonyl chloride, optionally in the presence of bases such as triethylamine or N-ethylmorpholine or N-methylpiperidine or dicyclohexylcarbodiimide and N-hydroxysuccinimide [cf. J. C. Sheehan, S. L. LEdis, J. Am. Chem. Soc. 95, 875 (1973); F. E. Frerman et al., J. Biol. Chem. 225, 507 (1982) and N. B. Benoton, K. Kluroda, Int. Pept. Prot. Res. 13, 403 (1979), 17, 187 (1981)].

The compounds of the general formulae (IVa), (IVb) and (IVc) are new and can be prepared by the abovementioned method.

The compounds of the general formula (V) are known [cf. Beilstein 5,19/5,24/5,29] or can be prepared from the corresponding alcohols or cycloalkenes by customary methods.

The compounds of the general formula (VI) are known [cf., for example, Beilstein 11/104].

The phenyl-substituted quinolines according to the invention can be employed as active substances in medicaments. The substances can act as inhibitors of enzymatic reactions in the context of arachidonic acid metabolism, in particular lipoxygenase.

They are thus preferred for the treatment and prevention of diseases of the respiratory tract such as allergies/asthma, bronchitis, emphysema, shock lung, pulmonary hypertension, inflammations/rheumatism and oedemas, thromboses and thromboembolisms, ischaemias (peripheral, cardiac, cerebral circulatory disorders), cardiac and cerebral infarcts, angina pectoris, arteriosclerosis, in tissue transplantation, dermatoses such as psoriasis, inflammatory dermatoses and for cytoprotection in the gastrointestinal tract.

The phenyl-substituted quinolines according to the invention can be used both in human medicine and in veterinary medicine.

The pharmacological effects of the substances according to the invention are determined by the following method:

As a measure of lipoxygenase inhibition, the release of leukotriene $B_4$ ($LTB_4$) in polymorphonuclear human leucocytes (PMN) was determined after addition of substances and Ca ionophore by means of reverse phase HPLC according to Borgeat, P. et. al., Proc. Nat. Acad. Sci. 76, 2148–2152 (1979).

The values obtained by this test for some compounds according to the invention are shown in Table 1 by way of

TABLE 1

| Example No. | 5-LO $IC_{50}$ ($\mu$mol/l) |
| --- | --- |
| 1 | 2.50 |
| 27 | 0.69 |
| 40 | 0.79 |
| 41 | 0.56 |

The present invention also includes pharmaceutical preparations which, in addition to inert, non-toxic, pharmaceutically suitable auxiliaries and excipients, contain one or more compounds of the general formula (I) or which consist of one or more active substances of the formula (I), and processes for the production of these preparations.

The active substances of the formula (I) should be present in these preparations in a concentration of 0.1 to 99.5% by weight, preferably of 0.5 to 95% by weight of the total mixture.

In addition to the active substances of the formula (I), the pharmaceutical preparations can also contain other pharmaceutical active substances.

The abovementioned pharmaceutical preparations can be prepared in a customary manner by known methods, for example with the auxiliary(ies) or excipient(s).

In general it has proved advantageous to administer the active substance(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired results.

However, it may be advantageous to deviate from the amounts mentioned, in particular depending on the type and the body weight of the subject to be treated, on individual behaviour towards the medicament, the nature and severity of the disease, the type of preparation and administration, and the time or interval at which administration takes place.

STARTING COMPOUNDS

Example I

Methyl 3-fluoro-5-hydroxyphenylacetate

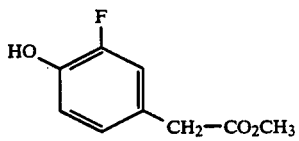

19.8 g (0.116 mol) of 3-fluoro-4-hydroxyphenylacetic acid are dissolved in 100 ml of methanol, 1 ml of conc. sulphuric acid is added and the mixture is heated to boiling for 2 h. After cooling, the solvent is evaporated in vacuo, the residue is taken up in 250 ml of dichloromethane and the solution is extracted twice with saturated $NaHCO_3$ solution. After drying, the organic phase is evaporated to dryness in vacuo and a viscous amber-coloured oil is obtained.

Yield: 18.4 g (85.8% of theory).

The examples shown in Table I are prepared in analogy to the procedure of Example I:

TABLE I

| Ex. No. | W | $R^1$ | $R^2$ | m.p. °C. | Yield (%) |
|---|---|---|---|---|---|
| II | H | Br | H | oil | 82.0 |
| III | H | $NO_2$ | H | 147 | quantitative |

Example IV

Methyl 2-(4-methallyloxyphenyl)-2-cyclopentyl-acetate

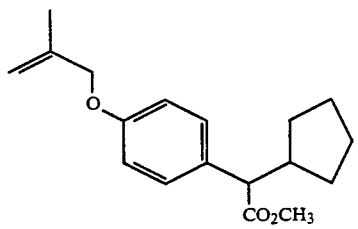

10 g (0.043 mol) of methyl 2-(4-hydroxyphenyl)-2-cyclopentyl-acetate are dissolved in 200 ml of dimethylformamide and 4.1 g (0.043 mol) of methallyl chloride and 5.9 (0.043 mol) of potassium carbonate are added with stirring. The mixture is allowed to react overnight at 100° C. After cooling, the solvent is evaporated in vacuo, the residue is taken up in 200 ml of dichloromethane, the solution is washed twice with 100 ml of water, the organic phase is dried using sodium sulphate and the product from evaporation in vacuo is purified by column chromatography (silica gel 60, eluent: toluene/ethyl acetate=100:5).

Yield: 7.66 g (61.9% of theory) of pale yellow oil.

EXAMPLE V

Methyl 2-(4-hydroxy-3-methallylphenyl)-2-cyclopentyl-acetate

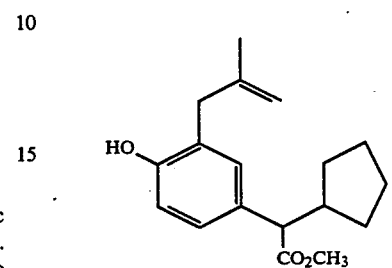

7.6 g (0.026 mol) of the compound from Example IV are dissolved in 50 ml of freshly distilled diethylaniline and the mixture is heated overnight at 200° C. (Claisen rearrangement). After cooling, the solvent is distilled off in vacuo, the residue is taken up in 200 ml of dichloromethane and the solution is washed twice with 40 ml of 2N hydrochloric acid in order to extract residues of diethylaniline. It is then washed until neutral, dried with sodium sulphate and concentrated to a small volume. Purification is carried out by column chromatography (silica gel 60, eluent: toluene/ethyl acetate=9:1).

Yield: 4.3 g (57.4% of theory) of pale yellow oil.

EXAMPLE VI

Methyl 2-(4-hydroxy-3-isobutylphenyl)-2-cyclopentyl-acetate

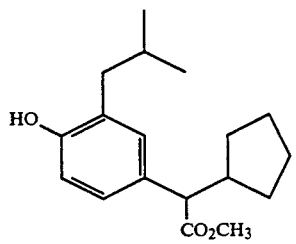

4 g (0.014 mol) of the compound from Example V are dissolved in 30 ml of methanol and 10 ml of acetic acid and hydrogenated at 5.3 bar using Pd/C as a catalyst. Reaction time: 2.5 h. After filtering off the catalyst, the solvent is evaporated in vacuo and a slightly yellowish oil is obtained.

Yield: 3.6 g (88.7% of theory).

EXAMPLE VII

Methyl 4-acetoxy-phenylacetate

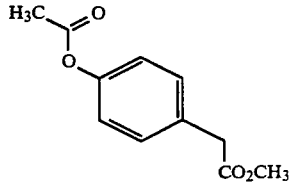

10 g (0.06 mol) of methyl 4-hydroxyphenylacetate are treated with 18.36 g (0.18 mol) of acetic anhydride (17 ml) and 1 ml of pyridine and the mixture is heated to boiling for 2 hours. The solvents are largely evaporated in vacuo, the residue is taken up in water and the solution is extracted with ethyl acetate. After drying using sodium sulphate, the solvent is distilled off in vacuo and a pale yellow, thin oil is obtained.

Yield: 12.3 g (98.6% of theory).

EXAMPLE VIII

Methyl 4-hydroxy-3-acetyl-phenylacetate

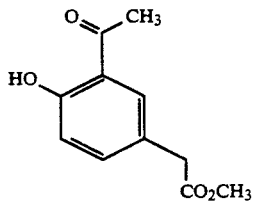

5.3 g of aluminum chloride are introduced under argon, 4 g (0.019 mol) of the compound from Example VII are added and the mixture is heated at 150° C. for 2 hours (Fries rearrangement). After cooling, 50 ml of dichloromethane are added, and the mixture is heated briefly to boiling and filtered. Purification is carried out by column chromatography (silica gel 60, eluent: toluene/ethyl acetate=8:2).

Yield: 2.4 g (60.7% of theory) of yellow oil.

The examples shown in Table II are prepared in analogy to the procedure of Example VII:

TABLE II

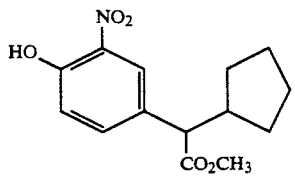

| Ex. No. | $R^1$ | $R^2$ | m.p. °C. | Yield (%) |
|---|---|---|---|---|
| IX | $H_3C$—CO— | H | oil | 86.8 |
| X | H | $H_3C$—CO— | oil | 96.0 |

EXAMPLE XI

Methyl 2-(4-hydroxy-3-nitrophenyl)-2-cyclopentyl-acetate

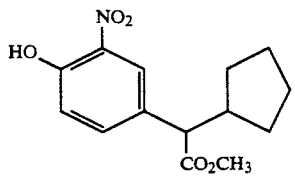

22.9 g (0.1 mol) of methyl 2-(4-hydroxyphenyl)-2-cyclopentyl-acetate are dissolved in 50 ml of $CH_2Cl_2$ and added dropwise at 5° C. to a solution of 50 ml of conc. $HNO_3$/50 ml of $H_2O$. The mixture is stirred for 15 min, then 100 ml of $H_2O$ are added and the organic phase is separated off. The aqueous phase is extracted three times with 50 ml of $CH_2Cl_2$, and the organic phases are washed 5 times with water, dried, concentrated to a small volume and filtered through silica gel. After concentration, the product is obtained in 71% yield (20 g). The product is further processed in crude form.

EXAMPLE XII

Methyl 2-(3-amino-4-hydroxy-phenyl)-2-cyclopentyl-acetate

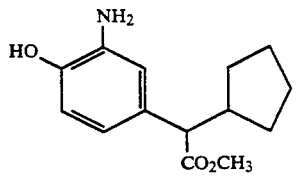

5.6 g (20 mmol) of the compound from Example XI are hydrogenated at 4 atm. in 100 ml of ethanol with the addition of 0.5 g of palladium/carbon (10% strength). The catalyst is filtered off with suction, the filtrate is concentrated and the residue is further reacted without further purification (quantitative yield).

EXAMPLE XIII

Methyl 2-(3-azido-4-hydroxy-phenyl)-2-cyclopentyl-acetate

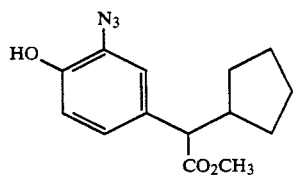

5.0 g (20 mmol) of the crude product from Example XII are dissolved in 20 ml of $H_2O$, 10 ml of ethanol and 20 ml of conc. HCl and the solution is diazotised at 0° C. with 1.8 g (26 mmol) of sodium nitrite in 10 ml of $H_2O$. After evolution of $N_2$ has ended, the mixture is extracted three times with 100 ml of $CH_2Cl_2$, the organic phases are concentrated and the residue is chromatographed on silica gel 60 ($CH_2Cl_2$/MeOH=100:2).

Yield: 4.5 g (82% of theory).

M.p.: 59°-60° C.

EXAMPLE XIV

Methyl 2-[3-fluoro-4-(quinolin-2-yl-methoxy)phenyl]acetate

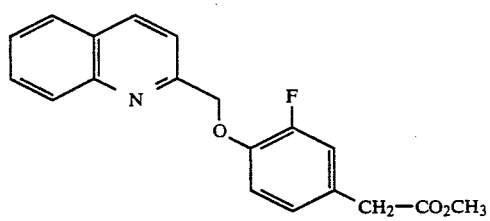

18.4 g (0.1 mol) of the compound from Example I are dissolved in 50 ml of DMF and 4 g (0.1 mol) of NaOH in 40 ml of methanol are added. 17.8 g (0.1 mol) of 2-chloromethylquinoline in 50 ml of DMF are added dropwise to this mixture with stirring and it is then heated at 100° C. for 5 h. After cooling, the solvent is evaporated in vacuo, the residue is taken up in dichloromethane, and the solution is washed twice with water, dried and concentrated in vacuo to a small volume.

Separation is carried out by column chromatography (silica gel 60, eluent: toluene/ethyl acetate=9:1 to 8:2).

Yield: 28 g (86% of theory) of yellow oil.

EXAMPLE XV

2-[3-Fluoro-4-(quinolin-2-yl-methoxy)phenyl]-acetic acid

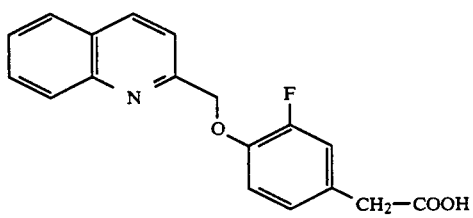

25 g (0.077 mol) of the compound from Example XIV are dissolved in 300 ml of methanol and 125 ml of 1 molar sodium hydroxide solution are added. The mixture is stirred at the boiling point for 3 h, allowed to cool and neutralised with 1N hydrochloric acid. The whole is evaporated to dryness in vacuo, and covered with 50 ml of water and with 150 ml of dichloromethane. The dichloromethane phase is dried and the solvent is evaporated in vacuo. Colourless crystals remain.

Yield: 19.5 g (81.5% of theory).
M.p.: 177°–179° C.

EXAMPLE XVI

2-[3-Fluoro-4-(quinolin-2-yl-methoxy)phenyl]-acetyl-methanesulphonamide

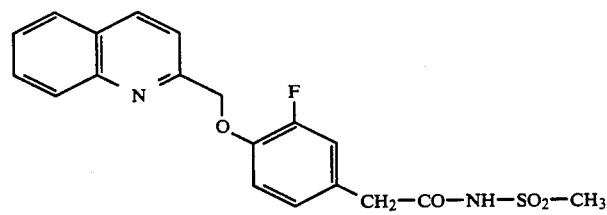

6 g (0.019 mol) of the compound from Example XV, 1.9 g (0.019 mol) of dried methanesulphonamide, 3.8 g (0.019 mol) of N-ethyl-N'-dimethylaminopropylcarbodiimide hydrochloride and 2.4 g (0.019 mol) of dimethylaminopyridine are dissolved in 40 ml of dichloromethane and the mixture is stirred at room temperature for 60 h. It is then evaporated to dryness in vacuo, the residue is taken up in 40 ml of dichloromethane and the solution is washed twice with 20 ml of water. After drying the organic phase using $Na_2SO_4$, it is evaporated in vacuo and the residue is separated by column chromatography (silica gel 60, eluent dichloromethane/ethyl acetate/glacial acetic acid=10:1:1).

Yield: 5.2 g (70.5% of theory) of colourless crystals.
M.p.: 171° C.

EXAMPLE XVII

2-[3-Fluoro-4-(quinolin-2-yl-methoxy)phenyl]-acetyl-benzylsulphonamide

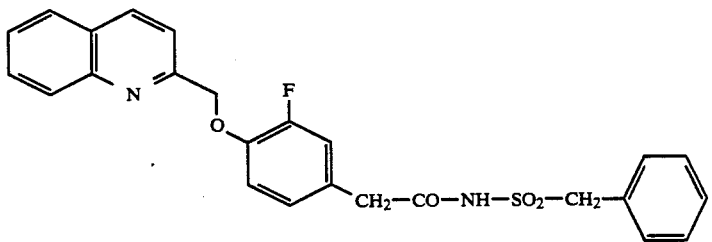

In analogy to Example XVI, the title compound is obtained from 4 g (0.013 mol) of the compound from Example XV, 2.22 g (0.013 mol) of dried benzylsulphonamide, 2.49 g (0.013 mol) of N-ethyl-N'-dimethylaminopropyl-carbodiimide hydrochloride and 1.59 g (0.013 mol) of dimethylaminopyridine.

Yield: 4.4 g (72.9% of theory) of colourless crystals.
M.p.: 156° C.

EXAMPLE XVIII

Methyl 2-[3-chloro-4-(quinolin-2-yl-methoxy)phenyl]acetate

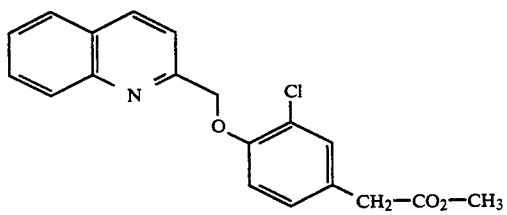

The title compound is prepared in analogy to the procedure of Example XIV from 5.3 g (0.03 mol) of 2-chloromethylquinoline, 6 g (0.03 mol) of methyl 3-chloro-4-hydroxyphenylacetate and 1.2 g (0.03 mol) of sodium hydroxide.

Yield: 8.7 g (84.9% of theory) of colourless crystal.
M.p.: 79° C.

EXAMPLE XIX

2-[3-Chloro-4-(quinolin-2-yl-methoxy)phenyl]-acetic acid

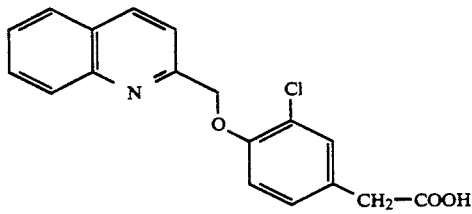

In analogy to the procedure of Example XV, the title compound is obtained from 4 g (0.012 mol) of the compound from Example XVIII and 18 ml of 1N sodium hydroxide solution.

Yield: 3.5 g (89.1% of theory) of colourless crystals.
M.p.: 203°–205° C.

EXAMPLE XX

Methyl 2-[3-bromo-4-(quinolin-2-yl-methoxy)phenyl]acetate

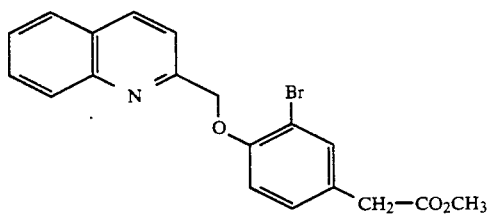

In analogy to the procedure of Example XIV, the title compound is prepared from 17 g (0.07 mol) of the compound from Example II, 12.32 g (0.07 mol) of 2-chloromethylquinoline and 2.8 g (0.07 mol) of sodium hydroxide.

Yield: 23.2 g (85.8% of theory) of slightly yellowish crystals.
M.p.: 90° C.

EXAMPLE XXI

2-[3-Bromo-4-(quinolin-2-yl-methoxy)phenyl]acetic acid

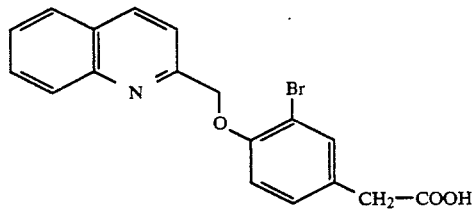

In analogy to the procedure of Example XV, the title compound is prepared from 3 g (7.77 mmol) of the compound from Example XX and 12 ml of 1N sodium hydroxide solution (12 mmol).

Yield: 2.5 g (86.5% of theory) of colourless crystals.
M.p.: 206°–208° C. (dec.).

EXAMPLE XXII

2-[3-Bromo-4-(quinolin-2-yl-methoxy)phenyl]acetylmethanesulphonamide

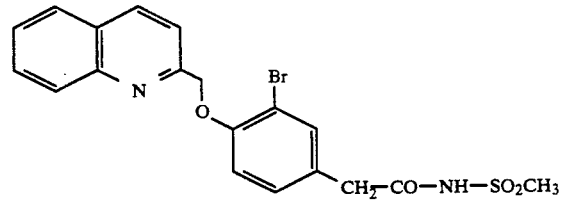

In anology to the procedure of Example XVI, the title compound is prepared from 2.8 g (7.5 mmol) of the compound from Example XXI, 0.71 g (7.5 mmol) of dried methanesulphonamide, 1.44 g (7.5 mmol) of N-ethyl-N'-dimethylaminopropylcarbodiimide hydrochloride and 0.92 g (7.5 mmol) of dimethylaminopyridine.

Yield: 0.86 g (25.5% of theory) of colourless crystals.
M.p.: 212° C. (dec.).

EXAMPLE XXIII

Methyl 2-[3-methoxy-4-(quinolin-2-yl-methoxy)phenyl]acetate

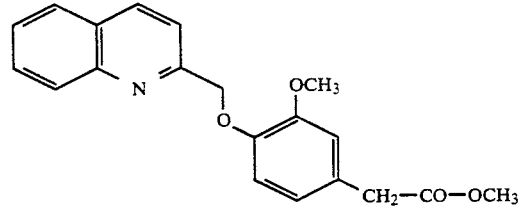

In analogy to the procedure of Example XIV, the title compound is prepared from 16 g (0.082 mol) of methyl 3-methoxy-4-hydroxyphenylacetate, 14.5 g (0.082 mol) of 2-chloromethylquinoline and 3.28 g (0.082 mol) of sodium hydroxide.

Yield: 20.5 g (74.1% of theory) of colourless crystals.
M.p.: 69° C.

Example XXIV

2-[3-Methoxy-4-(quinolin-2-yl-methoxy)phenyl]-acetic acid

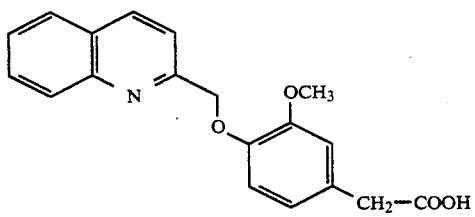

The title compound is prepared from 3 g (8.9 mmol) of the compound from Example XXIII and 12 ml of 1N sodium hydroxide solution analogously to the procedure of Example XV.

Yield: 2.4 g (83.4% of theory) of colourless crystals.
M.p.: 168°–170° C. (dec.).

Example XXV

Ethyl 2-[3-trifluoromethylthio-4-(quinolin-2-yl-methoxy)phenyl]acetate

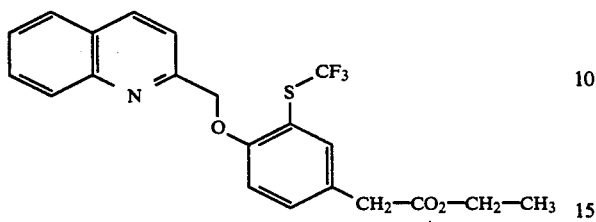

In analogy to the procedure of Example XIV, the title compound is prepared from 10 g (0.036 mol) of ethyl 4-hydroxy-3-trifluoromethylthiophenylacetate, 7.7 g (0.036 mol) of 2-chloromethylquinoline and 2.88 g (0.072 mol) of sodium hydroxide.

Yield: 7.55 g (49.8% of theory) of yellow oil.

Example XXVI

2-[3-Trifluoromethylthio-4-(quinolin-2-yl-methoxy)phenyl]acetic acid

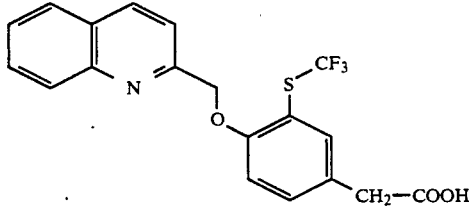

In analogy to the procedure of Example XV, the title compound is prepared from 2.1 g (5 mmol) of the compound from Example XXV and 0.4 g (0.01 mol) of sodium hydroxide in dioxane/water.

Yield: 1.8 g (91.6% of theory) of colourless crystals.
M.p.: 152° C.

Example XXVII

2-[3-Trifluoromethylthio-4-(quinolin-2-yl-methoxy)phenyl]acetyl-methanesulphonamide

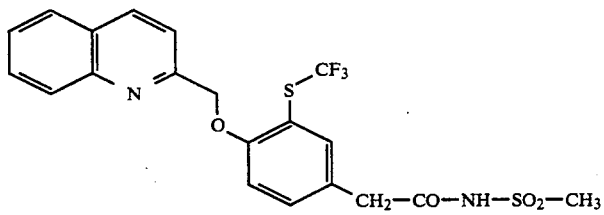

In analogy to the procedure of Example XV, the title compound is prepared from 1.2 g (3.1 mmol) of the compound from Example XXVI, 0.38 g (4 mmol) of methanesulphonamide, 0.77 g (4 mmol) of N-ethyl-N'-dimethylaminopropyl-carbodiimide hydrochloride and 0.49 g (4 mmol) of dimethylaminopyridine.

Yield: 1.2 g (82.4% of theory) of colourless crystals.
M.p.: 183° C. (dec.).

Example XXVIII

Methyl 2-[3-nitro-4-(quinolin-2-yl-methoxy)phenyl]acetate

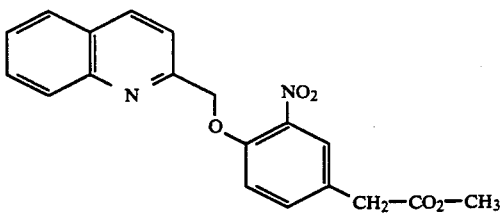

In analogy to the procedure of Example XIV, the title compound is prepared from 10.75 g (0.0509 mol) of the compound from Example III, 10.9 g (0.051 mol) of 2-chloromethylquinoline and 4.32 g (0.11 mol) of sodium hydroxide.

Yield: 3.3 g (18.4% of theory) of yellow crystals.
M.p.: 177° C.

Example XXIX

Methyl 2-[3-amino-4-(quinolin-2-yl-methoxy)phenyl]acetate

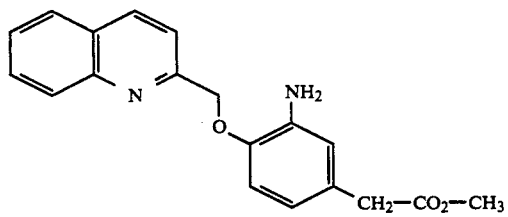

15 g (0.043 mol) of the compound from Example XXVIII are dissolved in 100 ml of tetrahydrofuran and 100 ml of methanol and 4 g (0.08 mol) of hydrazine monohydrate are added. Raney nickel is added in portions under argon with stirring, the temperature rising to 50° C. After the evolution of gas has ended, the mixture is heated to boiling for a further hour and then filtered while hot. The filtrate is concentrated in vacuo and the residual oil is taken up using 250 ml of dichloromethane. After washing twice using water and drying with sodium sulphate, the solvent is evaporated in vacuo and a colourless oil is obtained which crystallises overnight.

Yield: 12.5 g (90.3% of theory) of colourless crystals.
M.p.: 75° C.

Example XXX

Methyl 2-[3-(1-pyrryl)-4-(quinolin-2-yl-methoxy)phenyl]acetate

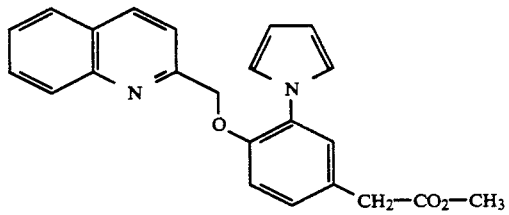

5 g (0.016 mmol) of the compound from Example XXIX are dissolved in 70 ml of acetic acid, 2.78 g (0.02 mol) of 2,5-dimethoxytetrahydrofuran are added and the mixture is heated to boiling for 2 hours. After distilling off the acetic acid in vacuo, taking up the residue in 200 ml of dichloromethane, extracting with water, drying with sodium sulphate and concentrating in vacuo to a small volume, the brown oil which remains (6 g) is separated by column chromatography (silica gel 60, eluent: toluene/ethyl acetate=4:1).

Yield: 3.2 g (53.8% of theory) of colourless crystals. M.p.: 102° C.

Example XXXI

2-[3-(1-Pyrryl)-4-(quinolin-2-yl-methoxy)phenyl]acetic acid

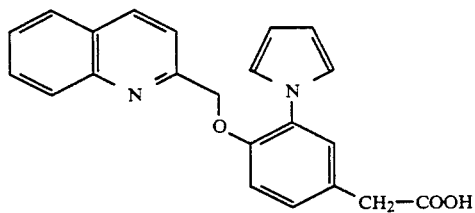

In analogy to the procedure of Example XV, the title compound is prepared from 0.8 g (2 mmol) of the compound from Example XXX and 0.2 g (5 mmol) of sodium hydroxide in 50 ml of isopropanol.

Yield: 0.7 g (97.8% of theory) of colourless crystals. M.p.: 173° C.

Example XXXII

Methyl 2-[3-vinyl-4-(quinolin-2-yl-methoxy)phenyl]acetate

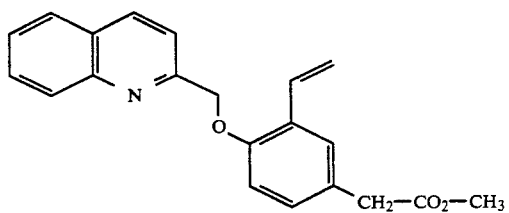

200 mg (0.21 mmol) of the catalyst [P(phenyl)$_3$]$_4$Pd are weighed into a 50 ml brown glass flask (flushed with argon) and 2 g (5.2 mmol) of the compound from Example XX and 1.4 ml (5.2 mmol) of Bu$_3$SnCH=CH$_2$ (d=1.086), both dissolved in 10 ml of toluene, are added under argon. The mixture is heated to boiling for 20 hours with stirring in a light-protected apparatus. The solvent is then evaporated in vacuo and the residue is separated by column chromatography (silica gel 60, eluent: toluene/ethyl acetate=4:1).

Yield: 1.5 g (86.6% of theory) of colourless crystals. M.p.: 69° C.

Example XXXIII

2-[3-Vinyl-4-(quinolin-2-yl-methoxy)phenyl]acetic acid

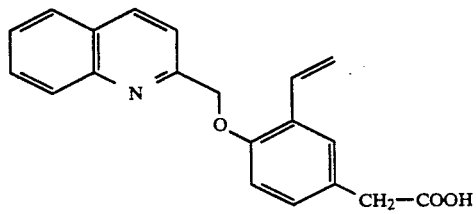

In analogy to the procedure of Example XV, the title compound is prepared from 1.1 g (3.3 mmol) of the compound from Example XXXII and 5 ml (5 mmol) of 1N sodium hydroxide solution.

Yield: 1.0 g (95.0% of theory) of colourless crystals. M.p.: 173° C.

Example XXXIV

Methyl 2-[3-ethyl-4-(quinolin-2-yl-methoxy)phenyl]acetate

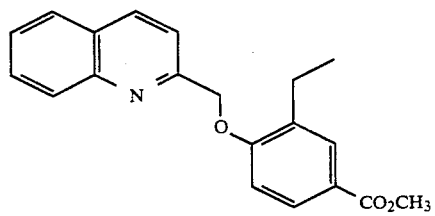

14.3 g (0.0429 mol) of the compound from Example XXXII are dissolved in 150 ml of methanol and 15 ml of glacial acetic acid, 1.5 g of 5% strength Pd-C are added, and the reaction mixture is heated to 30°-35° C. and hydrogenated. It is filtered through silica gel, the filtrate is concentrated in vacuo and the residue is recrystallised from isopropanol.

Yield: 8.5 g (59.1% of theory) or colourless crystals. M.p.: 72° C.

EXAMPLE XXXV

2-[3-Ethyl-4-(quinolin-2-yl-methoxy)phenyl]acetic acid

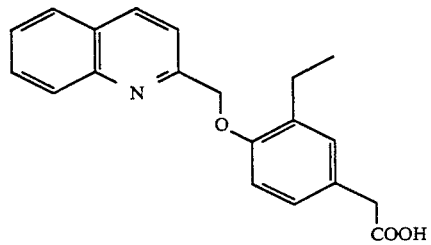

The title compound is prepared from 1.5 g (4.48 mmol) of the compound from Example XXXIV and 10 ml (10 mmol) of 1N sodium hydroxide solution analogously to the procedure of Example V.

Yield: 1.4 g (97.4% of theory) of colourless crystals. M.p.: 144° C.

EXAMPLE XXXVI

N-[3-Ethyl-4-(quinolin-2-yl-methoxy)phenyl]acetylmethanesulphonamide

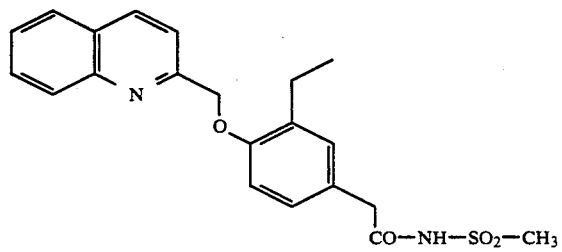

Analogously to the procedure of Example XVI, the title compound is prepared from 1.7 g (5.3 mmol) of the compound from Example XXXV, 0.6 g (6 mmol) of methanesulphonamide, 1.2 g (6 mmol) of N-methyl-N'-dimethylaminopropylcarbodiimide hydrochloride and 0.8 g (6 mmol) of dimethylaminopyridine.

Yield: 1.4 g (66.3% of theory) of colourless crystals. M.p.: 170° C.

EXAMPLE XXXVII

Methyl 2-[3-allyl-4-(quinolin-2-yl-methoxy)phenyl]acetate

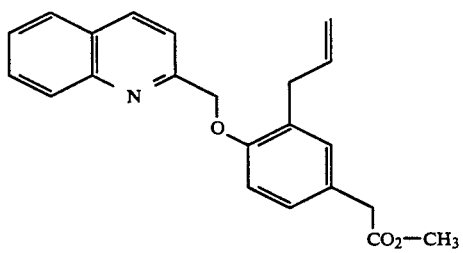

In analogy to the procedure of Example XXXII, the title compound is prepared from 16.6 g (0.043 mol) of the compound from Example XX, 13.6 g (0.043 mol) of $Bu_3$—Sn—$CH_2$—CH=$CH_2$ and 2.0 g (0.0017 mol) of [P(phenyl)$_3$]$_4$Pd.

Yield: 7.6 g (50.9% of theory) of colourless crystals. M.p. 71° C.

EXAMPLE XXXVIII

2-[3-Allyl-4-(quinolin-2-yl-methoxy)phenyl]acetic acid

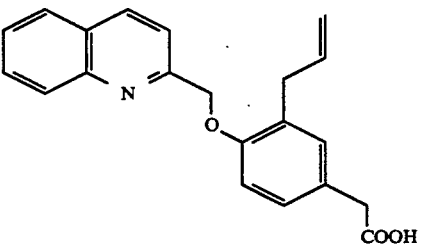

In analogy to the procedure of Example XV, the title compound is prepared from 2.0 g (5.8 mmol) of the compound from Example XXXVII and 10 ml (10 mmol) of 1N sodium hydroxide solution.

Yield: 1.7 g (88.0% of theory) of colourless crystals. M.p.: 130° C.

EXAMPLE XXXIX

Methyl 2-[3-propyl-4-(quinolin-2-yl-methoxy)phenyl]acetate

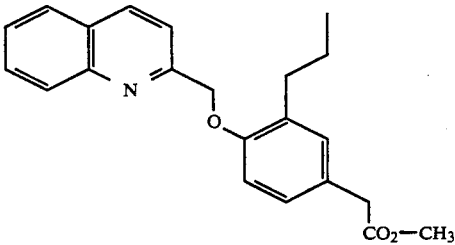

In analogy to the procedure of Example XXXIV, the title compound is prepared from 7.5 g (0.0225 mol) of the compound from Example XXXVII and 0.8 g of Pd/C (5%) using hydrogen.

Yield: 6.5 g (82.8% of theory) of yellowish oil.

EXAMPLE XL

2-[3-Propyl-4-(quinolin-2-yl-methoxy)phenyl]acetic acid

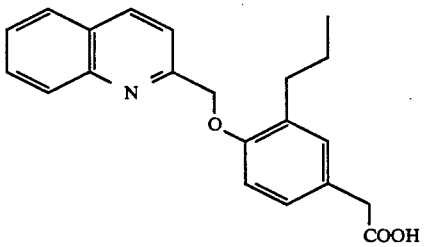

In analogy to the procedure of Example XV, the title compound is prepared from 1.5 g (4.3 mmol) of the compound from Example XXXIX and 10 ml (10 mmol) of 1N sodium hydroxide solution.

Yield: 1.4 g (97.2% of theory) of colourless crystals. M.p.: 135° C.

EXAMPLE XLI

2-[3-Propyl-4-(quinolin-2-yl-methoxy)phenyl]-acetyl-methanesulphonamide

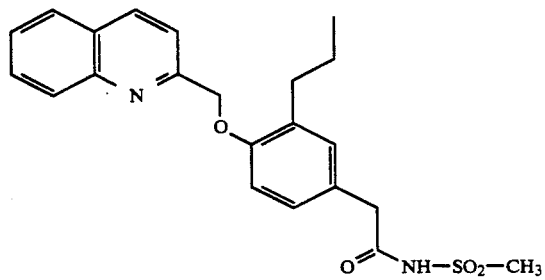

In analogy to the procedure of Example XVI, the title compound is prepared from 1.7 g (5.1 mmol) of the compound from Example XL, 0.6 g (6 mmol) of methanesulphonamide, 1.2 g (6 mmol) of N-ethyl-N'-dimethylaminocarbodiimide hydrochloride and 0.8 g (6 mmol) of dimethylaminopyridine.

Yield: 1.5 g (71.4% of theory) of colourless crystals. M.p.: 155° C. (dec.).

EXAMPLE XLII

Methyl 2-[3-acetyl-4-(quinolin-2-yl-methoxy)phenyl]acetate

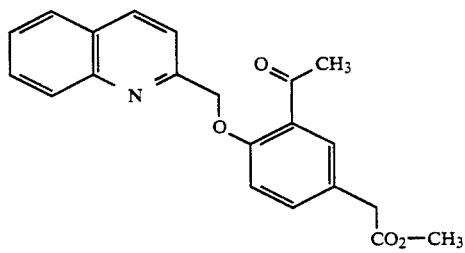

In analogy to the procedure of Example XIV, the title compound is prepared from 2.9 g (0.014 mol) of the compound from Example VIII, 2.5 g (0.014 mol) of 2-chloromethylquinoline and 0.56 g (0.014 mol) of sodium hydroxide.

Yield: 2.1 g (43.0% of theory) of colourless oil.

EXAMPLE XLIII

2-[3-Acetyl-4-(quinolin-2-yl-methoxy)phenyl]acetic acid

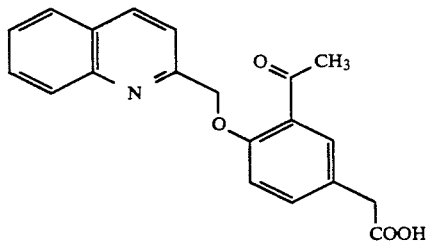

In analogy to the procedure of Example XV, the title compound is prepared from 1 g (2.9 mmol) of the compound from Example XLII and 0.13 g (5.8 mmol) of lithium hydroxide in 10 ml of water.

Yield: 0.7 g (72.1% of theory) of colourless crystals. M.p.: 119° C. (dec.).

PREPARATION EXAMPLES (GENERAL FORMULA I)

EXAMPLE 1

Methyl 2-[3-fluoro-4-(quinoline-2-methoxy)phenyl]-2-cyclopentylacetate

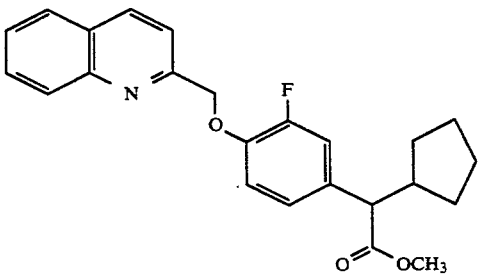

0.45 g (0.015 mol) of 80% pure NaH is suspended in DMF under argon, and 5 g (0.015 mmol) of the compound from Example XIV in 80 ml of DMF are added to the mixture. After evolution of hydrogen has ended, the mixture is subsequently additionally stirred for 1 h. 2.4 g=1.61 ml (0.015 mol) of cyclopentyl bromide in 100 ml of DMF are then added dropwise in the course of 1 h and the mixture is allowed to react further overnight. The solvent is evaporated to dryness in vacuo, the residue is taken up in dichloromethane, the solution is extracted with dilute hydrochloric acid and $NaHCO_3$ solution, dried and concentrated to a small volume, and the mixture is separated by column chromatography (silica gel 60, eluent: toluene/ethyl acetate=9:1).

Yield: 3.5 g (59.3% of theory) of colourless crystals. M.p.: 75° C.

EXAMPLE 2

Methyl 2-[3-methoxy-4-(quinolin-2-yl-methoxy)phenyl]-2-cyclooctylacetate

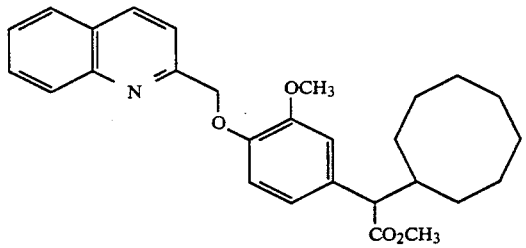

7.68 g (23 mmol) of the compound from Example XXIII and 4.4 g (23 mmol) of cyclooctyl bromide are dissolved in 100 ml of dimethylformamide. 3.36 g (30 mmol) of potassium tertiary butoxide, dissolved in 30 ml of DMF, are added dropwise to this mixture at 0°-10° C. with stirring. The mixture is subsequently stirred at room temperature for a further two hours and then treated with 30 ml of 1N hydrochloric acid. The solvent is then evaporated in vacuo, the residue is taken up in 200 ml of dichloromethane and the dichloromethane solution is washed twice with 100 ml of water. After drying with sodium sulphate, it is concentrated to a small volume in vacuo and the residue is separated by column chromatography (silica gel 60, eluent: toluene-/ethyl acetate=4:1).

Yield: 5.8 g (56.4% of theory) of yellow oil.

The compounds shown in Table 1 are prepared in analogy to the procedures of Examples 1 and 2:

TABLE 1

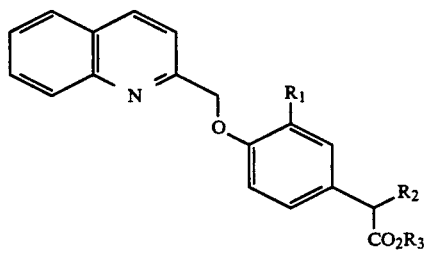

| Ex. No. | R¹ | R² | R³ | m.p. (°C.) | Yield (% of theory) |
|---|---|---|---|---|---|
| 3 | F | 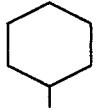 | CH₃ | 95 | 40.9 |
| 4 | F | 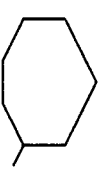 | CH₃ | 85 | 53.4 |
| 5 | Cl |  | CH₃ | oil | 43.3 |
| 6 | Cl |  | CH₃ | oil | 30.8 |
| 7 | Cl |  | CH₃ | oil | 67 |
| 8 | Br |  | CH₃ | 108–110 | 28.8 |
| 9 | Br |  | CH₃ | | 19.2 |
| 10 | Br |  | CH₃ | oil | 48 |

TABLE 1-continued

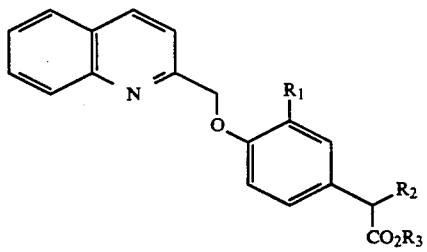

| Ex. No. | R¹ | R² | R³ | m.p. (°C.) | Yield (% of theory) |
|---|---|---|---|---|---|
| 11 | OCH₃ | | CH₃ | oil | 23.3 |
| 12 | OCH₃ | | CH₃ | oil | 43.5 |
| 13 | OCH₃ | | CH₃ | oil | 39.6 |
| 14 | | | CH₃ | oil | 82.2 |
| 15 | | | CH₃ | oil | 28.9 |
| 16 | | | CH₃ | oil | 60.8 |
| 17 | | | CH₃ | oil | 30.5 |
| 18 | | | CH₃ | oil | 61.8 |
| 19 | | | CH₃ | oil | 50.4 |

1:1

TABLE 1-continued

![structure: quinoline-CH2-O-phenyl(R1)-CH(R2)-CO2R3]

| Ex. No. | R¹ | R² | R³ | m.p. (°C.) | Yield (% of theory) |
|---|---|---|---|---|---|
| 20 | n-propyl | cyclopentyl | CH₃ | oil | 75.6 |
| 21 | n-propyl | cyclohexyl | CH₃ | oil | 35.0 |
| 22 | n-propyl | cycloheptyl | CH₃ | oil | 86.7 |
| 23 | sec-butyl | cyclopentyl | CH₃ | oil | 81.7 |
| 24 | —CO—CH₃ | cyclopentyl | CH₃ | 127 | 71.9 |
| 25 | N₃ | cyclopentyl | CH₃ | 102–104 | 77 |
| 26 | —NO₂ | cyclopentyl | CH₃ | 91–93 | 71.4 |

EXAMPLE 27

2-[3-Fluoro-4-(quinolin-2-yl-methoxy)phenyl]-2-cyclopentylacetic acid

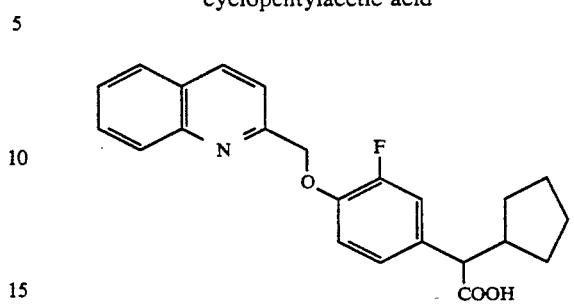

In analogy to the procedure of Example XV, the title compound is prepared from 2.5 g (0.00635 mol) of the compound from Example 1 and 9.35 ml of 1 molar sodium hydroxide solution (0.00935 mol)

Yield: 1.9 g (78.8% of theory) of colourless crystals.
M.p.: 143°–145° C.

The compounds shown in Table 2 were prepared in analogy to the procedure of Example 27:

TABLE 2

![structure: quinoline-CH2-O-phenyl(R1)-CH(R2)-CO2H]

| Ex. No. | R¹ | R² | m.p. (°C.) | Yield (% of theory) |
|---|---|---|---|---|
| 28 | F | cyclohexyl | 188–190 | 62.1 |
| 29 | F | cycloheptyl | 145 | 90.1 |
| 30 | Cl | cyclopentyl | 195 | 94.4 |
| 31 | Cl | cyclohexyl | 175 | 97.7 |
| 32 | Cl | cycloheptyl | 158–160 | 95.5 |

TABLE 2-continued
| Ex. No. | R¹ | R² | m.p. (°C.) | Yield (% of theory) |
|---|---|---|---|---|
| 33 | Br |  | 108–110 | 92.1 |
| 34 | Br |  | 165 | 58.9 |
| 35 | Br |  | 177 | 74.9 |
| 36 | OCH₃ |  | 197 | 66.6 |
| 37 | OCH₃ | 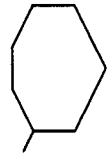 | 197–199 | 72.4 |
| 38 | OCH₃ | 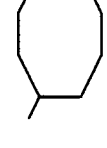 | 174 | 80.0 |
| 39 | OCH₃ | 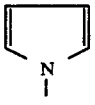 | 167 | 94.2 |
| 40 | 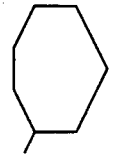 |  | 165 | 96.3 |
| 41 |  |  | 170 | 99.5 |
TABLE 2-continued
| Ex. No. | R¹ | R² | m.p. (°C.) | Yield (% of theory) |
|---|---|---|---|---|
| 42 |  |  | 133 | 98.6 |
| 43 |  |  | 153 | 90.3 |
| 44 |  |  | 136 | 89.9 |
| 45 |  |  | 161 | 95.4 |
| 46 |  1:1 |  | 133 | 97.2 |
| 47 |  | | 136 | 92.2 |
| 48 |  | | 159 | 94.1 |
| 49 |  |  | 129 | 97.1 |

TABLE 2-continued

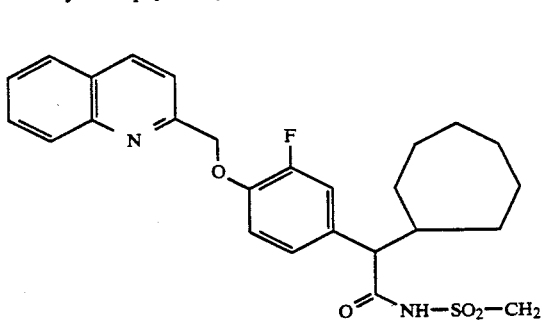

| Ex. No. | R¹ | R² | m.p. (°C.) | Yield (% of theory) |
|---|---|---|---|---|
| 50 | sec-butyl | cyclopentyl | 120 | 85.6 |
| 51 | —CO—CH₃ | cyclopentyl | 210 | 85.7 |
| 52 | N₃ | cyclopentyl | 76–79 | 65 |

EXAMPLE 53

{2-[3-Fluoro-(4-quinolin-2-yl-methoxy)phenyl]-2-cycloheptylacetyl}-methanesulphonamide

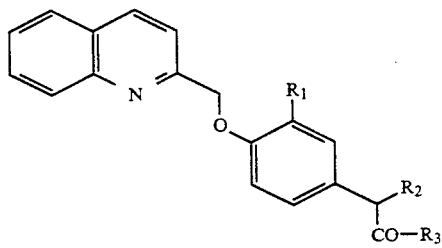

In analogy to the procedure of Example XVI, the title compound is prepared from 1.7 g (0.0042 mol) of the compound from Example 29, 0.4 g (0.042 mol) of dried methanesulphonamide, 0.81 g (0.0042 mol) of N-ethyl-N'-dimethylaminopropylcarbodiimide hydrochloride and 0.51 g (0.0042 mol) of dimethylaminopyridine.

The compounds shown in Table 3 are prepared in analogy to the procedure of Example 53:

TABLE 3

| Ex. No. | R¹ | R² | R³ | m.p. (°C.) | Yield (% of theory) |
|---|---|---|---|---|---|
| 54 | F | cyclohexyl | —NH—SO₂—CH₂—C₆H₅ | 105 | 83.3 |
| 55 | Cl | cyclopentyl | —NH—SO₂—CH₂—C₆H₅ | 184 | 66.4 |
| 56 | Cl | cyclohexyl | —NH—SO₂—CH₃ | 80 | 66 |
| 57 | Cl | cycloheptyl | —NH—SO₂—CH₂—C₆H₅ | 188 | 77 |

TABLE 3-continued

| Ex. No. | R¹ | R² | R³ | m.p. (°C.) | Yield (% of theory) |
|---|---|---|---|---|---|
| 58 | Br | cyclohexyl | $-NH-SO_2-CH_3$ | 189 | 63.2 |
| 59 | OCH₃ | cyclohexyl | $-NH-SO_2-CH_3$ | 130 | 79.7 |
| 60 | OCH₃ | cyclooctyl | $-NH-SO_2-CH_3$ | 123 | 59.7 |
| 61 | OCH₃ | cyclooctyl | $-NH-SO_2-CH(CH_3)_2$ | 103 | 80.8 |
| 62 | N-methylpyrrolyl | cyclohexyl | $-NH-SO_2-CH_3$ | 196–198 | 77 |
| 63 | propenyl | cyclohexyl | $-NH-SO_2-CH_3$ | 157 | 56.4 |
| 64 | ethyl | cyclohexyl | $-NH-SO_2-CH_3$ | 143 | 74.7 |
| 65 | propyl | cyclohexyl | $-NH-SO_2-CH_3$ | 147 | 70.7 |
| 66 | sec-butyl | cyclopentyl | $-NH-SO_2-CH_3$ | 97 | 79.5 |
| 67 | N₃ | cyclopentyl | $-NH-SO_2-(C_6H_5)\text{-p-J}$ | 63–67 | 11 |

The compounds shown in Table 4 were prepared in analogy to the procedure of Example 27:

TABLE 4

Structure: quinoline-2-CH$_2$-O-phenyl(R$_1$)-CH(R$_2$)-CO$_2$H

| Ex. No. | R$^1$ | R$^2$ | m.p. (°C.) | Yield (% of theory) |
|---|---|---|---|---|
| 68 | CH$_2$C(CH$_3$)$_2$– (branched alkyl) | cycloheptyl | 112 | 92.7 |
| 69 | CH$_2$C(CH$_3$)$_2$– | cycloheptyl | (−)-Enantiomer | |
| 70 | CH$_2$C(CH$_3$)$_2$– | cycloheptyl | (+)-Enantiomer | |

TABLE 4-continued

| Ex. No. | R$^1$ | R$^2$ | m.p. (°C.) | Yield (% of theory) |
|---|---|---|---|---|
| 71 | CH$_2$=C(CH$_2$CH$_3$)– | cyclopentyl | 123 | 75.1 |
| 72 | H$_3$C–CH(OCH$_3$)– | cyclopentyl | 115 (decomposition) | |
| 73 | H$_3$C–CH(OH)– | cycloheptyl | foam | 47.9 |

The compounds shown in Table 5 were prepared in analogy to the procedure of Example 53:

TABLE 5

Structure: quinoline-2-CH$_2$-O-phenyl(R$_1$)-CH(R$_2$)-CO-R$_3$

| Ex. No. | R$^1$ | R$^2$ | R$^3$ | m.p. (°C.) | Yield (% of theory) |
|---|---|---|---|---|---|
| 74 | CH$_2$CH$_3$ | cyclopentyl | –NH–SO$_2$–CH$_3$ | 140 | 58.0 |
| 75 | CH$_2$C(CH$_3$)$_2$– | cycloheptyl | –NH–SO$_2$–CH$_3$ | amorphous | 27 |
| 76 | CH$_2$C(CH$_3$)$_2$– | cycloheptyl | –NH–SO$_2$–C$_6$H$_4$–CH$_3$ | 189 | 89.2 |
| 77 | CH$_2$=C(CH$_2$CH$_3$)– | cyclopentyl | –NH–SO$_2$–C$_6$H$_4$–CH$_3$ | amorphous | 95 |

TABLE 5-continued

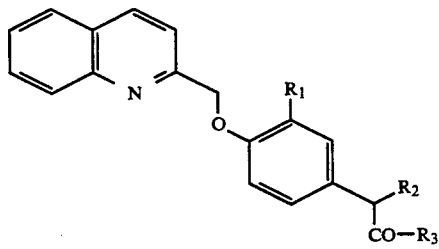

| Ex. No. | R[1] | R[2] | R[3] | m.p. (°C.) | Yield (% of theory) |
|---|---|---|---|---|---|
| 78 | ![allyl] | ![cyclopentyl] | —NH—SO$_2$—CH$_3$ | amorphous | 92.3 |

The compounds shown in Table 6 were prepared in analogy to the procedure of Example 2:

TABLE 6

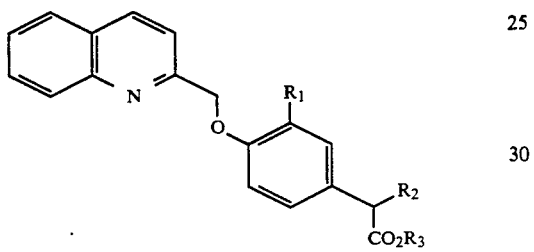

| Ex. No. | R[1] | R[2] | R[3] | m.p. (°C.) | Yield (% of theory) |
|---|---|---|---|---|---|
| 79 | ![allyl] | ![cyclopentyl] | —CH$_3$ | oil | 95.2 |

EXAMPLE 80

Methyl 2-[3-isobutyl-4-(quinolin-2-yl-methoxy)phenyl]-2-cyclohexylacetate

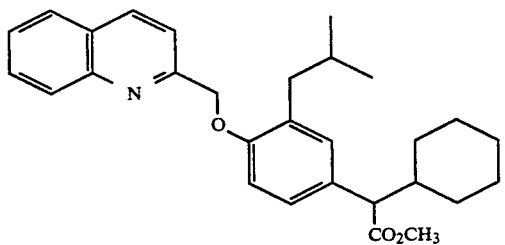

12 g (0.003 mol) of methyl 2-[3-isobutyl-4-(quinolin-2-yl-methoxy)phenyl]acetate and 6.52 g (0.04 mol)=4.9 ml of cyclohexyl bromide are dissolved in 36 ml of DMF under an argon atmosphere and the solution is cooled to 0° C. 4.88 g (0.04 mol) of potassium tertiary butylate, dissolved in 80 ml of DMF, are added dropwise thereto with stirring. After a reaction time of about 2 hours the temperature is allowed to rise to RT and the mixture is acidified with 2N hydrochloric acid and evaporated to dryness in vacuo. The remaining residue is extracted with 100 ml of dichloromethane and 50 ml of water, the organic phase is separated off, dried with Na$_2$SO$_4$, evaporated to a small volume in vacuo and the remaining residue is separated by column chromatography (silica gel 60, mobile solvent: dichloromethane/ethyl acetate=100/2).

Yield: 13 g (88.4% of theory) of a slightly yellowish oil.

Example 81

2-[3-Isobutyl-4-(quinolin-2-yl-methoxy)phenyl]-2-cyclohexyl-acetic acid

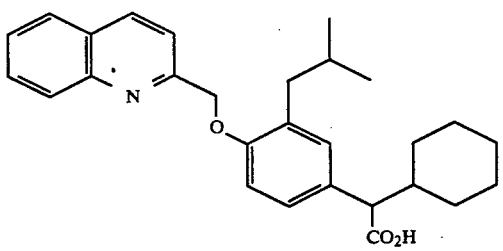

10.2 g (0.0236 mol) of the compound of Example 80 are taken up in 70 ml of 2-propanol and the solution is heated to boiling point overnight with 50 ml of 1N sodium hydroxide solution. After the mixture has become cold it is neutralised with 50 ml of 1N hydrochloric acid. The precipitate obtained is filtered off with suction, washed and dried and then recrystallised from diisopropyl ether.

Yield: 9.5 g (96.3% of theory) of colourless crystals. M.p: 130° C.

Example 82 and Example 83

(+)-2-[3-Isobutyl-4-(quinolin-2-yl-methoxy)phenyl]-2-cyclohexylacetic acid (Example 82)

(−)-2-[3-Isobutyl-4-(quinolin-2-yl-methoxy)phenyl]-2-cyclohexylacetic acid (Example 83)

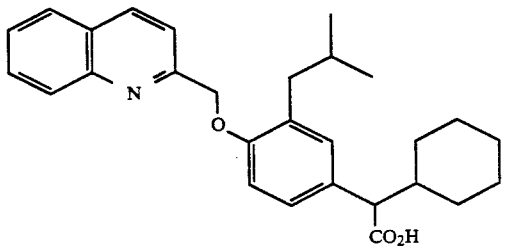

The title compounds are obtained by separating the racemate (Example 81) by chromatographic separation on chiral columns.

(+)-enantiomer:
  spec. rot: 17.96 (CHCl₃) (Example 82)
  mol. rot: 77.41
(−)-enantiomer:
  spec. rot: −18.86 (CHCl₃) (Example 83)
  mol. rot: −81.28

Example 84

Methyl 2-[3-isobutyl-4-(quinolin-2-yl-methoxy)phenyl]-2-cycloheptylacetate

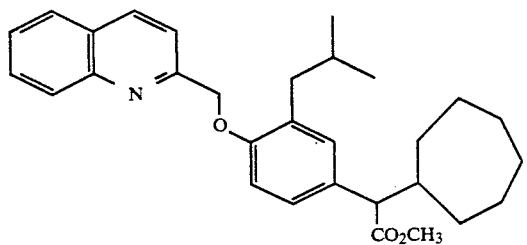

10 g (0.0275 mol) of methyl 2-[3-isobutyl-4-(quinolin-2-yl-methoxy)phenyl]acetate are reacted, in analogy to the procedure of Example 1, with 10.04 g (0.055 mol) of cycloheptyl bromide and 6.17 g (0.055 mol) of potassium tertiary butylate to give the title compound.

Yield: quantitative—a yellowish brown oil.

Examples 85 and 86

(+)-2-[3-Isobutyl-4-(quinolin-2-yl-methoxy)phenyl]-2-cyclopentylacetic acid (Example 85)

(−)-2-[3-Isobutyl-4-(quinolin-2-yl-methoxy)phenyl]-2-cyclopentylacetic acid (Example 86)

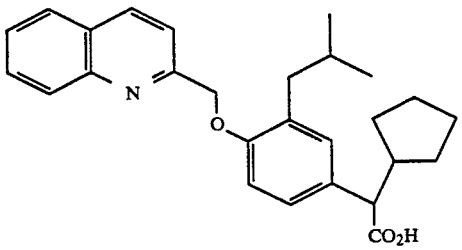

The title compounds are obtained in analogy to the procedure of Examples 82 and 83 by chromatographic separation of the compound of Example 50.

(+)-enantiomer:
  spec. rot: 44.56 (THF), Example 85
  mol. rot: 185.84
(−)-enantiomer:
  spec. rot: −41.07 (THF), Example 86
  mol. rot: −171.28

PREPARATION EXAMPLES

Example 87

N-Methanesulphonyl-2-[3-isobutyl-4-(quinolin-2-yl-methoxy)phenyl]-2-cyclohexylacetamide

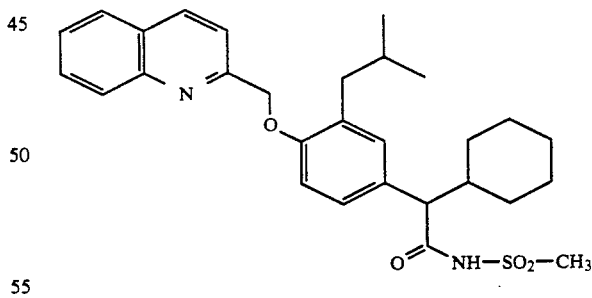

The title compound is prepared in analogy to the procedure of Example XVI from 3.5 g (0.008 mol) of the compound of Example 81, 1 g (0.008 mol) of mesyl chloride, 0.912 g of methanesulphonamide, 1.62 g (0.016 mol) of triethylamine and 0.98 g (0.008 mol) of dimethylaminopyridine.

Yield: 3.48 g (84.9% of theory) of a colourless amorphous powder.

M.p: 163°–170° C.

Example 88 and Example 89

(+)-N-Methanesulphonyl-2-[3-isobutyl-4-(quinolin-2-yl-methoxy)phenyl]-2-cyclohexylacetamide (Example 88)

(−)-N-Methanesulphonyl-2-[3-isobutyl-4-(quinolin-2-yl-methoxy)phenyl]-2-cyclohexylacetamide (Example 89)

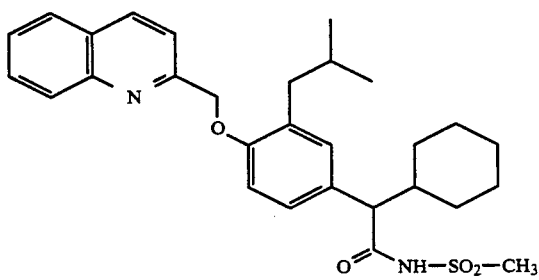

The two enantiomers are obtained by column-chromatographic separation of the compound of Example 87 on HPLC-HP 1050 Chiralcel OD in a solvent system of 86% n-hepane and 14% of a 2-propanol mixture containing 1% water +0.2% trifluoroacetic acid.

(+)-enantiomer:
  spec. rot: +32.15 (CHCl₃) Example 88
  mol. rot: +163.32
(−)-enantiomer:
  spec. rot: −28.96 (CHCl₃) Example 89
  mol. rot: −147.12

The pure enantiomers listed in Table 6 can either be prepared in analogy to the procedures of Examples 88 and 89 by separation of the racemate or by using the corresponding enantiomerically pure carboxylic acids.

TABLE 6

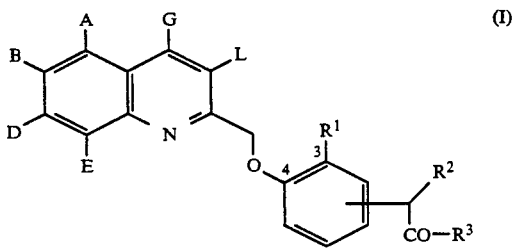

| Example No. | R¹ | Enantiomer | mol. rot. | spec. rot. |
|---|---|---|---|---|
| 90 | cyclopentyl | (+) | | |
| 91 | cyclopentyl | (−) | | |
| 92 | cycloheptyl | (+) | +147.99 (CHCl₃) | +28.35 (CHCl₃) |

TABLE 6-continued

| Example No. | R¹ | Enantiomer | mol. rot. | spec. rot. |
|---|---|---|---|---|
| 93 | cycloheptyl | (−) | −169.91 (CHCl₃) | −32.55 (CHCl₃) |

We claim:
1. 2-substituted quinolines of the formula

$$\text{(I)}$$

in which
A represents hydroxyl, halogen, cyano, carboxyl, nitro, trifluoromethyl, trifluoromethoxy or
  represents straight-chain or branched alkyl or alkoxy each having up to 8 carbon atoms, or represents aryl having 6 to 8 carbon atoms, which is optionally substituted by halogen, hydroxyl, nitro or cyano,
$R^1$ represents halogen, cyano, nitro, azido, trifluoromethyl, trifluoromethoxy or trifluoromethylthio, or
  represents straight-chain or branched alkoxy or acyl each having up to 8 carbon atoms, or
  represents straight-chain or branched alkyl having up to 8 carbon atoms, which is optionally substituted by hydroxyl or alkoxy having up to 6 carbon atoms, or
  represents aryl having 6 to 10 carbon atoms, or
  represents straight-chain or branched alkenyl having up to 6 carbon atoms, or represents a group of the formula $-NR^4R^5$, in which
    $R^4$ and $R^5$ are identical or different and denote hydrogen, straight-chain or branched alkyl having up to 8 carbon atoms, phenyl, acetyl or benzoyl, or
$R^1$ represents a member selected from the group consisting of pyrryl, pyrazolyl, pyridyl, pyrimidyl, pyrazinyl, pyridazinyl, furyl and thienyl,
$R^2$ represents cycloalkyl or -alkenyl having 3 to 12 carbon atoms,
$R^3$ represents a radical of the formula $-OR^6$ or $NR^7-SO_2-R^8$,
  in which R⁶ denotes hydrogen, straight-chain or branched alkyl having up to 8 carbon atoms, or phenyl, R⁷ denotes hydrogen or straight-chain or branched alkyl having up to 6 carbon atoms, and R⁸ denotes aryl having 6 to 10 carbon atoms, which is optionally mono- or disubstituted by identical or different substituents from the series comprising halogen, cyano, hyroxyl, nitro, trifluoromethyl, trifluoromethoxy, trifluoromethylthio, or by straight-chain or branched alkyl or alkoxy each having up to 8 carbon atoms, or denotes straight-chain or branched alkyl having up to 8 carbon atoms, which is optionally substituted by phenyl, which in turn can be substituted by halogen, cyano, nitro, trifluoromethyl, trifluoromethoxy, trifluoromethylthio or hydroxyl, or by straight-chain or branched alkyl or alkoxy each having up to 6 carbon atoms, and their physiologically acceptable salts.

2. 2-Substituted quinolines according to claim 1, in which

A, B, D, E, G and L are identical or different and represent hydrogen, hydroxyl, fluorine, chlorine, bromine, carboxyl, nitro, trifluoromethyl, trifluoromethoxy or represent straight-chain or branched alkyl or alkoxy each having up to 6 carbon atoms, or represent phenyl which is optionally substituted by fluorine, chlorine, bromine, hydroxyl, nitro or cyano, R¹ represents fluorine, chlorine, bromine, iodine, cyano, nitro, azido, trifluoromethyl, trifluoromethoxy, or represents straight-chain or branched alkoxy or acyl each having up to 6 carbon atoms, or represents straight-chain or branched alkyl having up to 6 carbon atoms, which is optionally substituted by hydroxyl or alkoxy having up to 4 carbon atoms, or represents straight-chain or branched alkenyl having up to 4 carbon atoms, or represents a group of the formula —NR⁴R⁵, in which R⁴ and R⁵ are identical or different and denote hydrogen or straight-chain or branched alkyl having up to 4 carbon atoms, or R¹ represents pyrryl, pyridyl, furyl or phenyl, R² represents cycloalkyl having 3 to 12 carbon atoms, R³ represents a radical of the formula —OR⁶ or —NR⁷—SO₂—R⁸, in which R⁶ denotes hydrogen or straight-chain or branched alkyl having up to 6 carbon atoms, R⁷ denotes hydrogen or straight-chain or branched alkyl having up to 4 carbon atoms, R⁸ denotes phenyl which is optionally substituted by fluorine, chlorine, bromine, iodine, cyano or by straight-chain or branched alkyl or alkoxy each having up to 6 carbon atoms, or denotes straight-chain or branched alkyl having up to 6 carbon atoms, which is optionally substituted by phenyl which can in turn be substituted by fluorine, chlorine, bromine or trifluoromethyl or by straight-chain or branched alkyl or alkoxy each having up to 4 carbon atoms and their physiologically acceptable salts.

3. 2-Substituted quinolines according to claim 1, in which

A, B, D, E, G and L are identical or different and represent hydrogen, hydroxyl, fluorine, chlorine, bromine or straight-chain or branched alkyl having up to 4 carbon atoms, R¹ represents fluorine, chlorine, bromine, nitro, azido or trifluoromethoxy, or represents straight-chain or branched alkoxy or acyl each having up to 4 carbon atoms, or represents straight-chain or branched alkyl having up to 4 carbon atoms, which is optionally substituted by hydroxyl or methoxy, or represents straight-chain or branched alkenyl having up to 4 carbon atoms, or represents a group of the formula —NR⁴R⁵, in which R⁴ and R⁵ are identical or different and denote hydrogen or straight-chain or branched alkyl having up to 3 carbon atoms, or R¹ represents pyrryl, furyl or phenyl, R² represents cyclobutyl, cyclopentyl, cyclohexyl, cycloheptyl or cyclooctyl, R³ represents a radical of the formula —OR⁶ or —NR⁷—SO₂—R⁸, in which R⁶ denotes hydrogen or straight-chain or branched alkyl having up to 4 carbon atoms, R⁷ denotes hydrogen, methyl or ethyl, R⁸ denotes phenyl which is optionally substituted by methyl, fluorine, chlorine, bromine, iodine, methoxy or trifluoromethyl, or denotes straight-chain or branched alkyl having up to 4 carbon atoms, which is optionally substituted by phenyl which can in turn be substituted by fluorine, chlorine, bromine, methyl or methoxy and their physiologically acceptable salts.

4. A compound according to claim 1 wherein such compound is 2-[3-isobutyl-4-(quinoline-2-yl-methoxy)-phenyl]-2-cyclopentyl-acetic acid of the formula

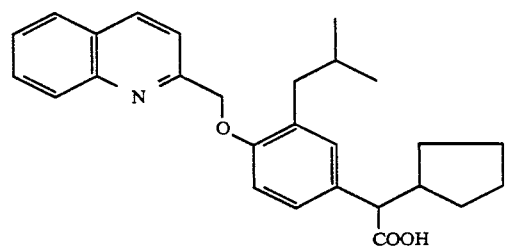

or physiologically acceptable a salt thereof.

5. A compound according to claim 1 wherein such compound is {2-[3-propyl-4-(quinoline-2-yl-methoxy)-phenyl]-2-cycloheptyl-acetic acid} methan sulfonamide of the formula

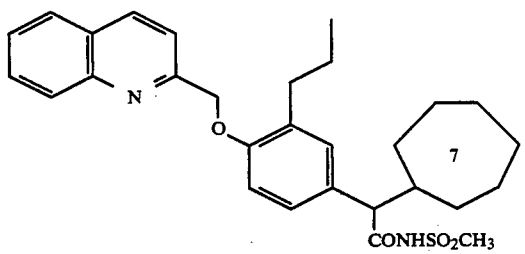

or physiologically acceptable a salt thereof.

6. A compound according to claim 1 wherein such compound is {2-[3-isobutyl-4-(quinoline-2-yl-methoxy)-phenyl]-2-cyclopentyl-acetic acid} methan sulfonamide of the formula

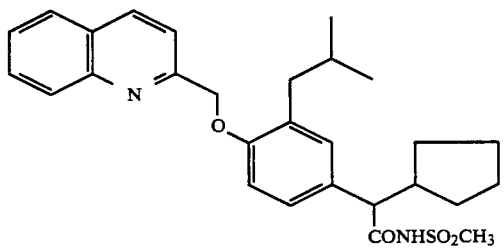

or physiologically acceptable a salt thereof.

7. A compound according to claim 1 wherein such compound is. 2-[3-isobutyl-4-(quinoline-2-yl-methoxy)-phenyl]-2-cycloheptyl-acetic acid of the formula

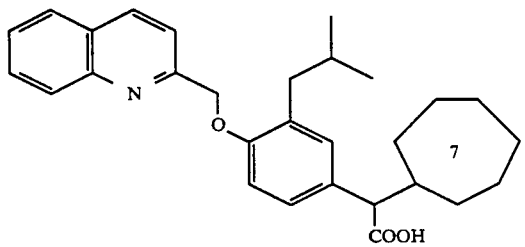

or physiologically acceptable a salt thereof.

8. A compound according to claim 1 wherein such compound is {2-[3-isobutyl-4-(quinoline-2-yl-methoxy)-phenyl]-2-cycloheptyl-acetic acid} methan sulfonamide of the formula

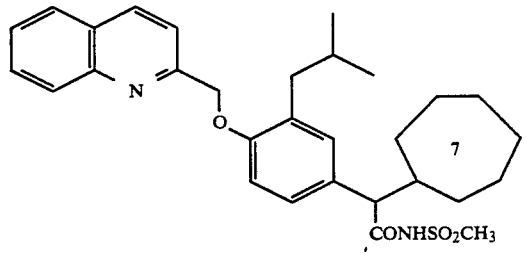

or physiologically acceptable a salt thereof.

9. A compound according to claim 1 wherein such compound is N-Methanesulphonyl-2-[3-isobutyl-4-(quinolin-2-yl-methoxy)phenyl]-2-cyclohexyl-acetamide of the formula

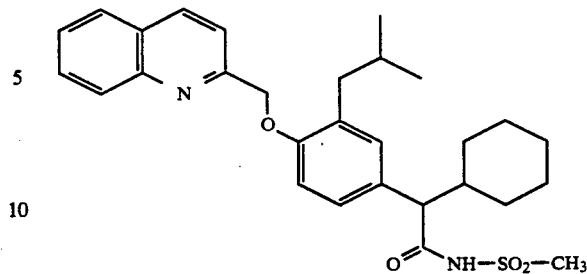

or physiologically acceptable a salt thereof.

10. A compound according to claim 1 wherein such compound is (+)-N-Methanesulphonyl-2-[3-isobutyl-4-(quinolin-2-yl-methoxy)phenyl]-2-cyclohexyl-acetamide of the formula

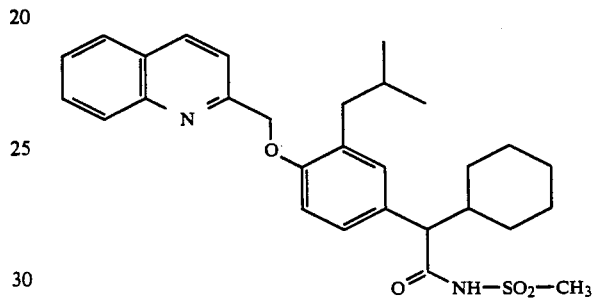

or a salt thereof.

11. A compound according to claim 1 wherein such compound is (−)-N-Methanesulphonyl-2-[3-isobutyl-4-(quinolin-2-yl-methoxy)phenyl]-2-cyclohexyl-acetamide of the formula

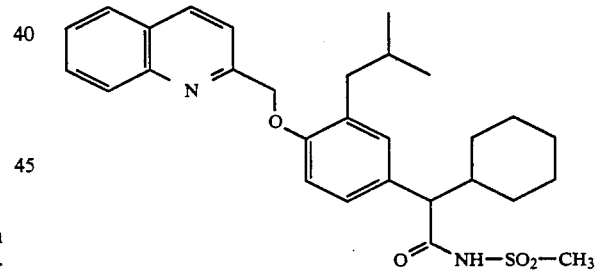

or a physiologically acceptable a salt thereof.

12. A compound according to claim 1 wherein such compound is (+)-N-Methanesulphonyl-2-[3-isobutyl-4-(quinolin-2-yl-methoxy)phenyl-]-2-cycloheptyl-acetamide formula

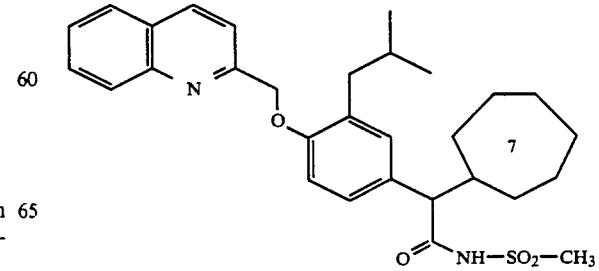

13. A compound according to claim 1 wherein such compound is (−)-N-Methanesulphonyl-2-[3-isobutyl-4-(quinolin-2-yl-methoxy)phenyl]-2-cycloheptyl-acetamide of the formula

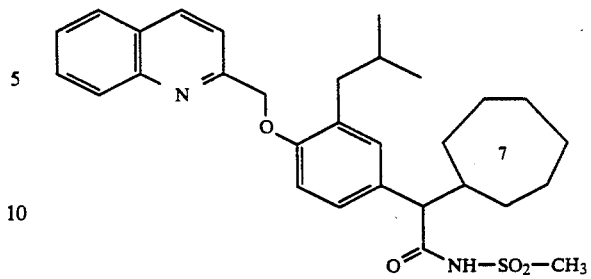

or physiologically acceptable a salt thereof.

14. A composition for the treatment of allergies/asthma, bronchitis, emphysema, shock lung, pulmonary hypertension, inflammations/rheumatism and oedemas, thromboses and thromboembolisms, ischaemias (peripheral, cardiac, cerebral circulatory disorders), cardiac and cerebral infarcts, angina pectoris, arteriosclerosis, in tissue transplantation, psoriasis, inflammatory dermatoses and for cytoprotection in the gastrointestinal tract comprising an amount effective therefor of a compound or salt thereof according to claim 1 and a pharmacologically acceptable diluent.

15. A method of inhibiting lipoxygenase in a patient in need thereof which comprises administering to such a patient an amount effective therefor of a compound or salt thereof according to claim 1.

* * * * *